United States Patent
Matsumoto et al.

(10) Patent No.: US 11,492,252 B2
(45) Date of Patent: Nov. 8, 2022

(54) METHOD FOR PRODUCING GROUP III-V SEMICONDUCTOR NANOPARTICLE, METHOD FOR PRODUCING GROUP III-V SEMICONDUCTOR QUANTUM DOT, AND FLOW REACTION SYSTEM

(71) Applicant: FUJIFILM Corporation, Tokyo (JP)

(72) Inventors: Hideki Matsumoto, Kanagawa (JP); Kenji Wada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 419 days.

(21) Appl. No.: 16/583,260

(22) Filed: Sep. 26, 2019

(65) Prior Publication Data
US 2020/0017358 A1  Jan. 16, 2020

Related U.S. Application Data

(63) Continuation of application No. PCT/JP2018/009684, filed on Mar. 13, 2018.

(30) Foreign Application Priority Data

Mar. 28, 2017  (JP) ................. JP2017-063603

(51) Int. Cl.
C09K 11/62 (2006.01)
B82B 3/00 (2006.01)
(Continued)

(52) U.S. Cl.
CPC ............... *B82B 3/00* (2013.01); *C01B 25/08* (2013.01); *C09K 11/62* (2013.01); *G01N 33/588* (2013.01);
(Continued)

(58) Field of Classification Search
CPC .......... B28B 3/00; B28B 3/0004; C09K 11/62; C09K 11/70; C01B 25/08
See application file for complete search history.

(56) References Cited

U.S. PATENT DOCUMENTS

2004/0025634 A1  2/2004 Nakamura et al.
2005/0220915 A1  10/2005 Nakamura et al.
(Continued)

FOREIGN PATENT DOCUMENTS

EP      2351702      8/2011
JP      2001335307   12/2001
(Continued)

OTHER PUBLICATIONS

Liang. Erythorbic acid promoted formation of CdS QDs in a tube-in-tube micro-channel reactor. Materials Research Bulletin vol. 60, Dec. 2014, pp. 552-555 (Year: 2014).*
(Continued)

*Primary Examiner* — Matthew E. Hoban
(74) *Attorney, Agent, or Firm* — JCIPRNET

(57) ABSTRACT

A method for producing a Group III-V semiconductor nanoparticle by flow reaction, including: introducing a solution of compound containing Group III element into a first flow channel, introducing a solution of compound containing Group V element into a second flow channel, and combining the solutions to produce nanoparticles, in which the combining portion is constituted by a multi-layered tubular mixer, one of the solutions is allowed to flow through a flow channel in the smallest tube of the mixer, and the other of the solutions is allowed to flow through a flow channel adjacent to the flow channel in the smallest tube, and a value of a ratio of linear velocity of the solution flowing in the flow channel adjacent to the flow channel in the smallest tube to linear velocity of the solution flowing in the flow channel in the smallest tube is a specific value.

7 Claims, 4 Drawing Sheets

(51) Int. Cl.
*C01B 25/08* (2006.01)
*G01N 33/58* (2006.01)
*H01L 21/02* (2006.01)
*H01L 29/06* (2006.01)
*B82Y 15/00* (2011.01)
*B82Y 30/00* (2011.01)
*B82Y 40/00* (2011.01)

(52) U.S. Cl.
CPC .... *H01L 21/02601* (2013.01); *H01L 29/0665* (2013.01); *B82Y 15/00* (2013.01); *B82Y 30/00* (2013.01); *B82Y 40/00* (2013.01); *C01P 2004/64* (2013.01)

(56) References Cited

U.S. PATENT DOCUMENTS

| | | | |
|---|---|---|---|
| 2009/0029563 A1 | 1/2009 | Hachiya | |
| 2009/0295005 A1 | 12/2009 | Rauscher et al. | |
| 2011/0229545 A1 | 9/2011 | Shum et al. | |
| 2013/0345440 A1 | 12/2013 | Severins et al. | |
| 2018/0273844 A1* | 9/2018 | Deshpande | C09K 11/623 |

FOREIGN PATENT DOCUMENTS

| | | |
|---|---|---|
| JP | 2003160315 | 6/2003 |
| JP | 2003160336 | 6/2003 |
| JP | 2003225900 | 8/2003 |
| JP | 2006096569 | 4/2006 |
| JP | 2007224233 | 9/2007 |
| JP | 2008037716 | 2/2008 |
| JP | 2013525087 | 6/2013 |
| JP | 2014004576 | 1/2014 |
| JP | 2014501229 | 1/2014 |
| WO | 2007086302 | 8/2007 |

OTHER PUBLICATIONS

Kim. Highly Luminescent InP/GaP/ZnS Nanocrystals and Their Application to White Light-Emitting Diodes. J. Am. Chem. Soc. 2012, 134, 8, 3804-3809 (Year: 2012).*
Li. High-throughput emulsification in a microporous tube-in-tube michrochannel device: O/W emulsion formation. Chemical Engineering Journal 228 (2013) 155-161 (Year: 2013).*
"Search Report of Europe Counterpart Application", dated Jan. 28, 2020, p. 1-p. 7.
"International Search Report (Form PCT/ISA/210) of PCT/JP2018/009684", dated May 22, 2018, with English translation thereof, pp. 1-5.
"Written Opinion of the International Searching Authority (Form PCT/ISA/237) of PCT/JP2018/009684", dated May 22, 2018, with English translation thereof, pp. 1-7.
"Notice of allowance of Japan Counterpart Application", with English translation thereof, dated May 12, 2020, p. 1-95.
"Office Action of Europe Counterpart Application", dated Apr. 15, 2021, p. 1-p. 5.
"Office Action of Korea Counterpart Application" with English translation thereof, dated Nov. 13, 2020, p. 1-p. 6.

* cited by examiner

METHOD FOR PRODUCING GROUP III-V SEMICONDUCTOR NANOPARTICLE, METHOD FOR PRODUCING GROUP III-V SEMICONDUCTOR QUANTUM DOT, AND FLOW REACTION SYSTEM

CROSS-REFERENCE TO RELATED APPLICATIONS

This application is a Continuation of PCT International Application No. PCT/JP2018/009684 filed on Mar. 13, 2018, which claims priority under 35 U.S.C. § 119 (a) to Japanese Patent Application No. 2017-063603 filed in Japan on Mar. 28, 2017. Each of the above applications is hereby expressly incorporated by reference, in its entirety, into the present application.

BACKGROUND OF THE INVENTION

1. Field of the Invention

The present invention relates to a method for producing a Group III-V semiconductor nanoparticle, a method for producing a Group III-V semiconductor quantum dot, and a flow reaction system.

2. Description of the Related Art

Semiconductor quantum dots are nanoscale (several nanometers to tens of nanometers) semiconductor crystals and exhibit characteristic light absorption and luminescence properties based on quantum size effects. The application range expected for semiconductor quantum dots is wide, and application research to displays, illuminations, biological imaging, solar cells, and the like is in progress based on the specific luminescence properties corresponding to the particle size. In addition, application research as a quantum dot laser, a single electron transistor, or the like, which realizes high luminance and low power consumption by utilizing unique electronic properties of semiconductor quantum dots, is also in progress.

Currently, the mainstream of semiconductor quantum dots is cadmium-based quantum dots using nanocrystals having cadmium as a cation (nanocrystals such as cdSe or CdS). However, there is concern about the toxicity of cadmium, and thus a need for non-cadmium-based quantum dots is growing. Quantum dots using nanocrystals of Group III-V semiconductors (hereinafter, referred to as "Group III-V semiconductor quantum dots") having indium or the like as a cation are known as non-cadmium-based quantum dots. However, Group III-V semiconductor quantum dots still have many problems in terms of performance.

Under such circumstances, technological development is underway to improve the performance of Group III-V semiconductor quantum dots. For example, JP2008-037716A discloses the preparation of InP fine particles using a flow reaction. In the technology disclosed in JP2008-037716A, an In raw material solution and a P raw material solution are combined in a flow channel with an inner diameter of 1 µm to 1 mm and heated at a relatively low temperature range while flowing in the flow channel to form InP fine particle precursors. Then, the liquid containing the InP fine particle precursors is exposed to a high temperature to obtain semiconductor fine particles having a uniform particle size.

SUMMARY OF THE INVENTION

In a case where semiconductor quantum dots are applied to a display or the like, higher color purity of luminescence leads to a wider color gamut that can be displayed, making it possible to display vivid images with high color reproducibility. Semiconductor quantum dots are generally considered to have a narrower luminescence peak half-width and higher color purity than organic luminescent materials. Nevertheless, Group III-V semiconductor quantum dots that have been reported so far, including the technology disclosed in above-mentioned JP2008-037716A, have not yet achieved sufficient color purity.

An object of the present invention is to provide a method for producing a Group III-V semiconductor nanoparticle, which makes it possible to obtain a Group III-V semiconductor quantum dot that exhibits a narrow luminescence peak half-width and sharp luminescence properties, and a flow reaction system suitable for carrying out such a method. Another object of the present invention is to provide a method for producing a Group III-V semiconductor quantum dot that exhibits a narrow luminescence peak half-width and sharp luminescence properties.

As a result of extensive studies in view of the foregoing objects, the present inventors have found that Group III-V semiconductor nanoparticles can be obtained which realize Group III-V semiconductor quantum dots that exhibit sharper luminescence properties than a case where homogeneous mixing using a T-shaped mixer is employed, by a configuration in which a combining portion where a solution of a compound containing a Group III element and a solution of a compound containing a Group V element are combined is constituted by a multi-layered tubular mixer; one of the two solutions is allowed to flow in a flow channel in the smallest tube of the mixer, and the other solution is allowed to flow in a flow channel adjacent to the flow channel in the smallest tube; and a specific difference is provided in a linear velocity of each solution flowing in the mixer, in the flow reaction of the production of a Group III-V semiconductor nanoparticle used as a core of a Group III-V semiconductor quantum dot. Further studies based on these findings have led to the completion of the present invention.

That is, the foregoing objects of the present invention are achieved by the following means.

[1] A method for producing a Group III-V semiconductor nanoparticle by a flow reaction, comprising:
 introducing a solution of compound a1 containing a Group III element into a first flow channel and introducing a solution of compound a2 containing a Group V element into a second flow channel;
 combining the solution of compound a1 flowing in the first flow channel and the solution of compound a2 flowing in the second flow channel in a combining portion; and
 reacting compound a1 and compound a2 while the combined liquid is flowing downstream to produce a Group III-V semiconductor nanoparticle,
 in which the combining portion is constituted by a multi-layered tubular mixer,
 one of the solution of compound a1 and the solution of compound a2 is allowed to flow through a flow channel in the smallest tube of the multi-layered tubular mixer, and the other one of the solutions is allowed to flow through a flow channel adjacent to the flow channel in the smallest tube, and
 a value of a ratio of linear velocity r2 of the solution flowing in the flow channel adjacent to the flow channel in the smallest tube to linear velocity r1 of the solution flowing in the flow channel in the smallest tube is 0.2 or less or 5.0 or more.

[2] The method for producing a Group III-V semiconductor nanoparticle according to [1], in which the Group III element is selected from In, Al, and Ga.

[3] The method for producing a Group III-V semiconductor nanoparticle according to [1] or [2], in which the Group V element is selected from P, N, As, and Sb.

[4] The method for producing a Group III-V semiconductor nanoparticle according to any one of [1] to [3], in which the Group III-V semiconductor nanoparticle is produced by setting the conditions for reacting compound a1 and compound a2 to 270° C. to 350° C. for 5 to 120 minutes.

[5] The method for producing a Group III-V semiconductor nanoparticle according to any one of [1] to [4], in which the multi-layered tubular mixer is a two-layered tubular mixer.

[6] The method for producing a Group III-V semiconductor nanoparticle according to any one of [1] to [5], in which an equivalent diameter of the smallest tube of the multi-layered tubular mixer is 0.1 to 2 mm.

[7] A method for producing a Group III-V semiconductor quantum dot, comprising:
obtaining a Group III-V semiconductor nanoparticle by the method for producing a Group III-V semiconductor nanoparticle according to any one of [1] to [6]; and
introducing Ga into a surface layer of the Group III-V semiconductor nanoparticle.

[8] A flow reaction system for producing a Group III-V semiconductor nanoparticle, comprising:
a first flow channel through which a solution of compound a1 containing a Group III element flows;
a second flow channel through which a solution of compound a2 containing a Group V element flows;
a combining portion in which the first flow channel and the second flow channel are combined; and
a reaction flow channel connected to a downstream side of the combining portion,
in which the combining portion is constituted by a multi-layered tubular mixer.

A numerical range represented using "to" in the present specification means a range including numerical values described before and after "to" as the lower limit value and the upper limit value, respectively.

The terms "upstream" and "downstream" in the present specification are used with respect to the direction of fluid flow, with the side into which fluid is introduced being upstream and the opposite side (the side from which the fluid flows out) being downstream.

The term "Group III-V semiconductor nanoparticle" in the present invention means a nanoparticle (nanocrystal) composed of a compound semiconductor consisting of a Group III element and a Group V element and additionally, it is used in a meaning including a form in which an element (for example, Zn) other than the crystal component is doped or introduced in the crystal structure or surface layer of the nanoparticle.

The term "nanoparticle" in the present specification means a particle having an average particle size of less than 20 nm, preferably 15 nm or less, and more preferably 10 nm or less. In addition, the average particle size of the "nanoparticle" is usually 1 nm or more and preferably 2 nm or more.

According to the method for producing a Group III-V semiconductor nanoparticle of the present invention, it is possible to obtain a group III-V semiconductor nanoparticle that can make a semiconductor quantum dot exhibit sharper luminescence properties in a case where the Group III-V semiconductor nanoparticle is used as a core of the semiconductor quantum dot. In addition, according to the method for producing a Group III-V semiconductor quantum dot of the present invention, it is possible to obtain a Group III-V semiconductor quantum dot exhibiting a narrow luminescence peak half-width and sharp luminescence properties.

In addition, the flow reaction system of the present invention is a system suitable for carrying out the method for producing a Group III-V semiconductor nanoparticle of the present invention.

DESCRIPTION OF THE PREFERRED EMBODIMENTS

The preferred embodiments of the present invention will be described below, but the present invention is not limited to these embodiments.

[Method for Producing Group III-V Semiconductor Nanoparticle]

In the method for producing a Group III-V semiconductor nanoparticle according to the embodiment of the present invention (hereinafter, simply referred to as "the method for producing a nanoparticle according to the embodiment of the present invention"), compound a1 containing a Group III element and compound a2 containing a Group V element are reacted using a specific flow reaction to obtain a desired Group III-V semiconductor nanoparticle.

More specifically, the combining portion of the solution of compound a1 and the solution of compound a2 in the flow reaction is constituted by a multi-layered tubular mixer, and one of the solution of compound a1 and the solution of compound a2 is allowed to flow through a flow channel in the smallest tube of the multi-layered tubular mixer and the other one of the solutions is allowed to flow in a flow channel adjacent to the flow channel in the smallest tube (space between the smallest tube and the tube adjacent to the smallest tube). In addition, a specific difference is provided in the linear velocity of each solution flowing in the multi-layered tubular mixer. By taking such a configuration, instantaneous uniform mixing of both solutions becomes possible, and the obtained Group III-V semiconductor nanoparticle can have desired properties.

The method for producing a nanoparticle according to the embodiment of the present invention will be described with reference to the accompanying drawings. The drawings are for the purpose of facilitating the understanding of the present invention, and the size or relative magnitude relationship of each member may be different in magnitude for the convenience of explanation and does not represent the actual relationship as it is. In addition, the present invention is not limited to these embodiments except as defined in the present invention.

Figure 1:
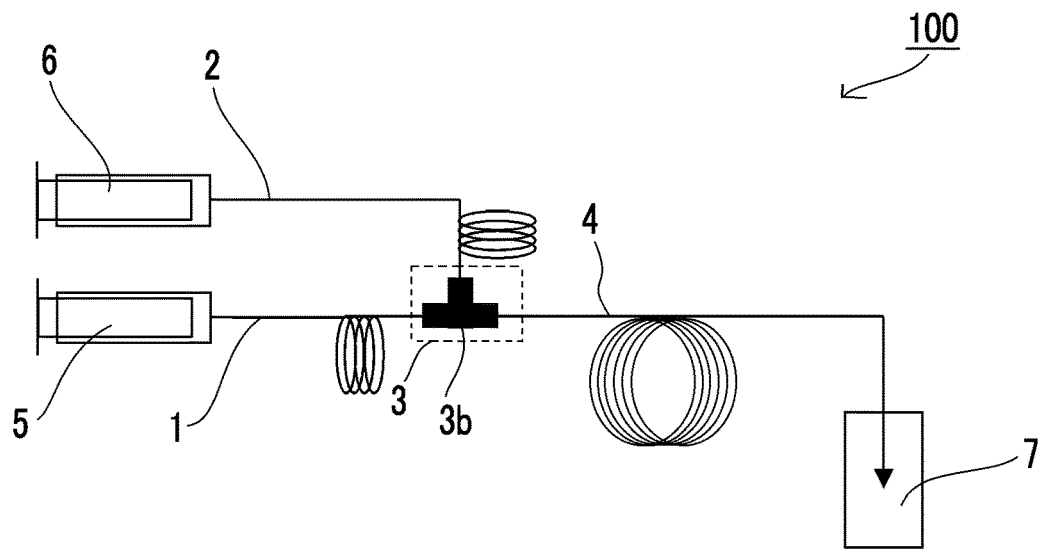
FIG. 1 is a view showing a preferred embodiment of a flow reaction system of the present invention.

A preferred flow reaction system (100) for carrying out the production method of the present invention is shown in FIG. 1. The flow reaction system (100) shown in FIG. 1 includes a first flow channel (1) through which the solution of compound a1 containing a Group III element flows, a second flow channel (2) through which the solution of compound a2 containing a Group V element flows, a combining region (3) in which the first flow channel (1) and the second flow channel (2) are combined, and a reaction flow channel (4) connected to the downstream side of the combining region (3).

In the embodiment of FIG. 1, a compound a1 solution introducing means (5) for introducing the solution of compound a1 into the first flow channel (1) is disposed upstream of the first flow channel (1); and a compound a2 solution introducing means (6) for introducing the solution of compound a2 into the second flow channel (2) is disposed upstream of the second flow channel (2). The compound a1 solution introducing means (5) and the compound a2 solution introducing means (6) are not particularly limited, and a variety of pumps can be used. As such pumps, a syringe pump, a plunger pump, a smooth flow pump, and the like can be used, and a syringe pump can be suitably used from the viewpoint of controlling the flow rate with high accuracy. The same applies to a third liquid introducing means (11) which will be described later.

In the embodiment of FIG. 1, a two-layered tubular mixer (3b), which is an embodiment of a multi-layered tubular mixer, is disposed in the combining region (3).

Figure 2:
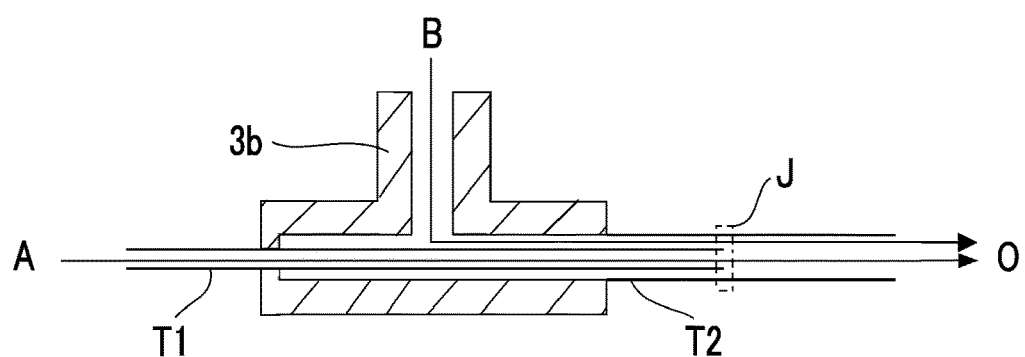
FIG. 2 is a cross-sectional view of a two-layered tubular mixer installed in a combining region in the embodiment of FIG. 1.

FIG. 2 is a cross-sectional view showing a state of solution combining using this two-layered tubular mixer (3b). The first flow channel (1) is connected to the A side (opening A) of the smallest tube (T1, inner tube) passing through the inside of the two-layered tubular mixer (3b), or the first flow channel (1) itself is integrated with the smallest tube (T1), whereby the solution of compound a1 flowing in the first flow channel (1) flows from the A side to the O side in the smallest tube (T1). In the present invention, the inside of the smallest tube is referred to as the flow channel in the smallest tube.

On the other hand, the second flow channel (2) is connected to an introduction portion B (opening B) of the two-layered tubular mixer (3b). As a result, the solution of compound a2 flowing in the second flow channel (2) fills the flow channel adjacent to the flow channel in the smallest tube of the two-layered tubular mixer (3b) (space between the smallest tube (T1) and the tube (T2, outer tube) adjacent to the smallest tube), and flows toward the O side.

The solution of compound a1 flowing in the smallest tube flow channel toward the O side is combined at the O-side end (combining portion J) of the smallest tube (T1) with the solution of compound a2 which has flowed toward the O side in the flow channel adjacent to the smallest tube flow channel, and the combined liquid is introduced into the reaction flow channel (4) which is connected to the downstream of the combining portion J.

Figure 3:
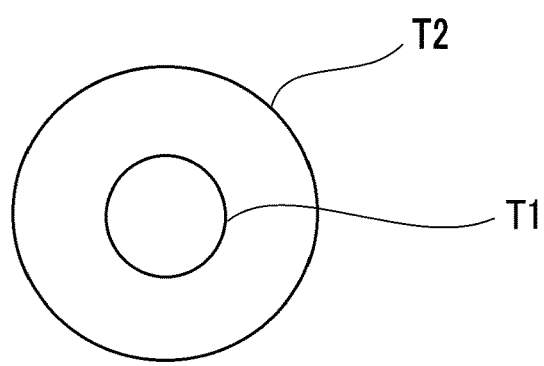
FIG. 3 is a view of a combining portion J of the two-layered tubular mixer of FIG. 2 as viewed from the O side.

FIG. 3 shows a cross section of the combining portion J in FIG. 2 as viewed from the O side. In FIG. 3, the solution of compound a1 flows in the smallest tube (T1), and the solution of compound a2 flows between the smallest tube (T1) and the tube (T2) adjacent to the smallest tube.

The compound a1 solution and the compound a2 solution are combined by the two-layered tubular mixer (3b), and compound a1 and compound a2 are reacted while the combined liquid is flowing downstream to produce a Group III-V semiconductor nanoparticle.

In the embodiment of FIG. 1, the value (r2/r1) of the ratio of the linear velocity r2 of the solution (solution of compound a2) flowing in the flow channel adjacent to the flow channel in the smallest tube of the two-layered tubular mixer (3b) to the linear velocity r1 of the solution (solution of compound a1) flowing in the flow channel in the smallest tube of the mixer is 0.2 or less, or 5.0 or more. Thus, by providing a specific difference in the linear velocity at which both solutions flow in the mixer, the semiconductor quantum dot prepared using the obtained Group III-V semiconductor nanoparticle as a core can be made to exhibit a narrow luminescence peak half-width and sharper luminescence properties. That is, it is possible to obtain a Group III-V semiconductor quantum dot with high color purity of luminescence.

The reason why the above effect is exhibited by setting the r2/r1 to 0.2 or less, or 5.0 or more is not clear, but it is presumed that, in a case where the r2/r1 is set to 0.2 or less, or 5.0 or more and then in a case where both solutions are combined in the mixer, the portion with higher linear velocity becomes a constant negative pressure state, and a draw-in flow occurs or thinning of the interface between both solutions occurs, so that it becomes possible to mix both solutions instantaneously (for example, about 50 ms) uniformly. That is, it is estimated that, in a case where the r2/r1 is set to 0.2 or less, or 5.0 or more, a crystal nucleus of a Group semiconductor can be formed in a state of extremely small concentration unevenness, and therefore the size of the formed nanoparticles is highly uniform.

The mere uniform mixing can also be realized by causing a turbulent flow at the combining portion using a T-shaped mixer or the like. However, in a case where a T-shaped mixer or the like is used, the interface at which the compound a1 solution and the compound a2 solution collide with each other comes in contact with the wall surface of the flow channel, and therefore crystals are easily precipitated on the wall surface of the flow channel starting from there. As a result, it is difficult to stably generate nanoparticles that achieve desired light luminescence properties, due to clogging of the flow channel. In the method for producing a nanoparticle according to the embodiment of the present invention, instantaneous uniform mixing is realized while preventing such precipitation of crystals on the wall surface of the flow channel using a multi-layered tubular mixer.

In a case where the r2/r1 is set to 0.2 or less, the lower limit thereof is not particularly limited. The r2/r1 is set to usually 0.005 or more and practically 0.01 or more. In a case where the r2/r1 is set to 5.0 or more, the upper limit thereof is not particularly limited. The r2/r1 is set to usually 200 or less and practically 100 or less. The r2/r1 can be adjusted by adjusting the flow rate of the solution introduced by the solution introducing means or adjusting the cross-sectional area of the flow channel in the mixer.

In the present invention, the unit of "linear velocity" is, for example, cm/minute, and in this case, the linear velocity is calculated by dividing the flow rate ($cm^3$/minute) of the solution sent by the solution sending means by the cross-sectional area ($cm^2$) of the flow channel through which the solution flows.

In the above embodiment, an embodiment has been described in which the solution of compound a1 is allowed to flow through the flow channel in the smallest tube, and the solution of compound a2 is allowed to flow in the flow channel adjacent to the flow channel in the smallest tube. However, the solution to be flowed in each flow channel may be reversed. That is, an embodiment in which the solution of compound a2 is allowed to flow in the flow channel in the smallest tube and the solution of compound a1 is allowed to flow in the flow channel adjacent to the flow channel in the smallest tube is also preferable as the embodiment of the method for producing a nanoparticle according to the embodiment of the present invention.

Figure 4:
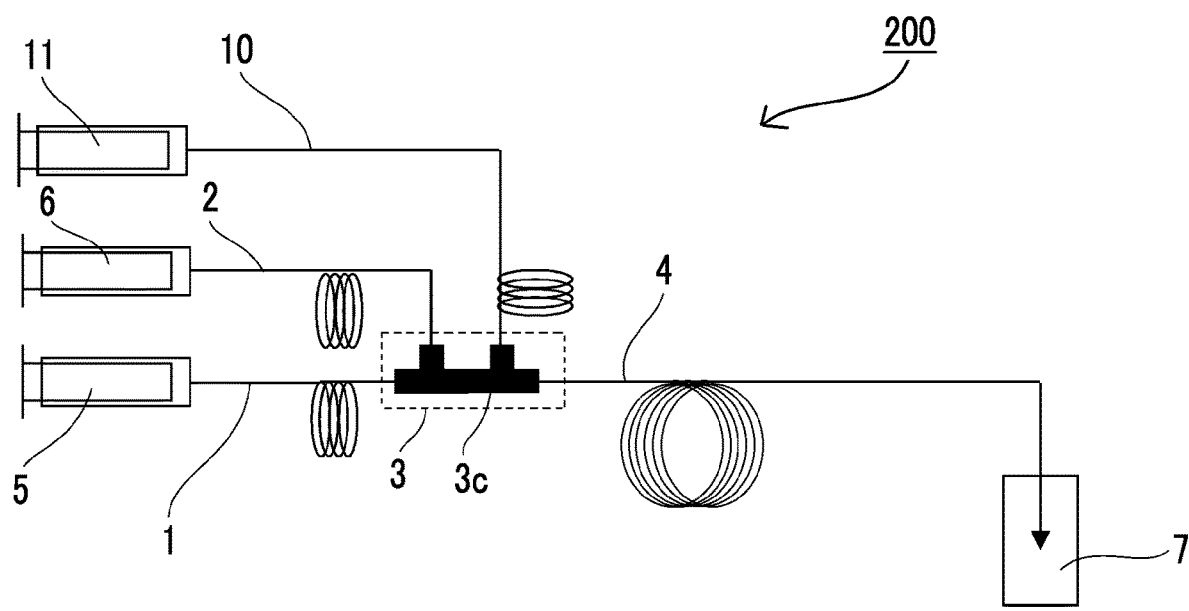
FIG. 4 is a view showing another preferred embodiment of the flow reaction system of the present invention.

Another preferred flow reaction system (200) for carrying out the method for producing a nanoparticle according to the embodiment of the present invention is shown in FIG. 4. The flow reaction system (200) shown in FIG. 4 includes a first flow channel (1) through which a solution of compound a1 flows, a second flow channel (2) through which a solution of compound a2 flows, and a third flow channel (10) through which a third solution described later flows, a combining region (3) where the first flow channel (1), the second flow channel (2), and the third flow channel (10) are combined, and a reaction flow channel (4) connected to the downstream of the combining region (3).

In the embodiment of FIG. 4, a compound a1 solution introducing means (5) for introducing the solution of compound a1 into the first flow channel (1) is disposed upstream of the first flow channel (1); a compound a2 solution introducing means (6) for introducing the solution of compound a2 into the second flow channel is disposed upstream of the second flow channel (2); and a third solution introducing means (11) for introducing the third solution into the third flow channel (10) is disposed upstream of the third flow channel (10).

Figure 5:
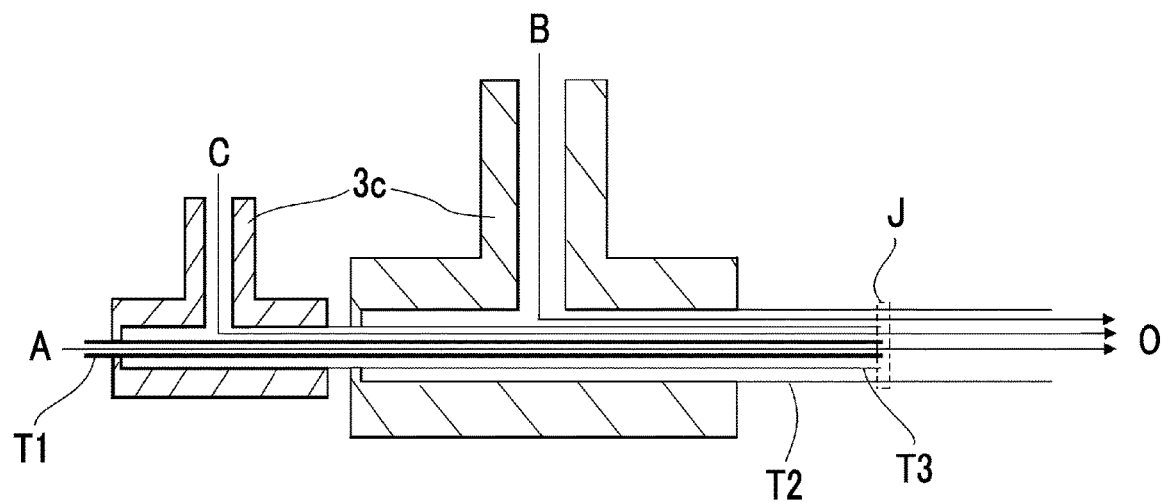
FIG. 5 is a cross-sectional view of a three-layered tubular mixer installed in the combining region in the embodiment of FIG. 4.

In the embodiment of FIG. 4, a three-layered tubular mixer (3c) is disposed in the combining region (3). FIG. 5 is a cross-sectional view showing solution combining using this three-layered tubular mixer (3c). The first flow channel (1) is connected to the A side (opening A) of the smallest tube (T1) passing through the inside of the three-layered tubular mixer (3c), or the first flow channel (1) itself is integrated with the smallest tube (T1), whereby the solution of compound a1 flowing in the first flow channel (1) flows from the A side to the O side in the smallest tube (T1). In the present invention, the inside of the smallest tube is referred to as the flow channel in the smallest tube.

In addition, the second flow channel (2) is connected to an introduction portion C (opening C) of the three-layered tubular mixer (3c). As a result, the solution of compound a2 flowing in the second flow channel (2) fills the flow channel adjacent to the flow channel in the smallest tube of the three-layered tubular mixer (3c) (space between the smallest tube (T1) and the tube (T3, middle tube) adjacent to the smallest tube (T1)), and flows toward the O side.

In addition, the third flow channel (10) is connected to an introduction portion B (opening B) of the three-layered tubular mixer (3c). As a result, the third liquid flowing in the third flow channel (10) fills the space between the tube (T3) adjacent to the smallest tube (T1) of the three-layered tubular mixer (3c) and the outermost tube (T2, outer tube), and flows toward the O side.

The solution of compound a1 flowing in the flow channel in the smallest tube toward the O side is combined at the O-side end (combining portion J) of the smallest tube (T1) with the solution of compound a2 which has flowed toward the O side in the flow channel adjacent to the flow channel in the smallest tube, and the combined liquid is introduced into the reaction flow channel (4) which is connected to the downstream of the combining portion J.

Figure 6:
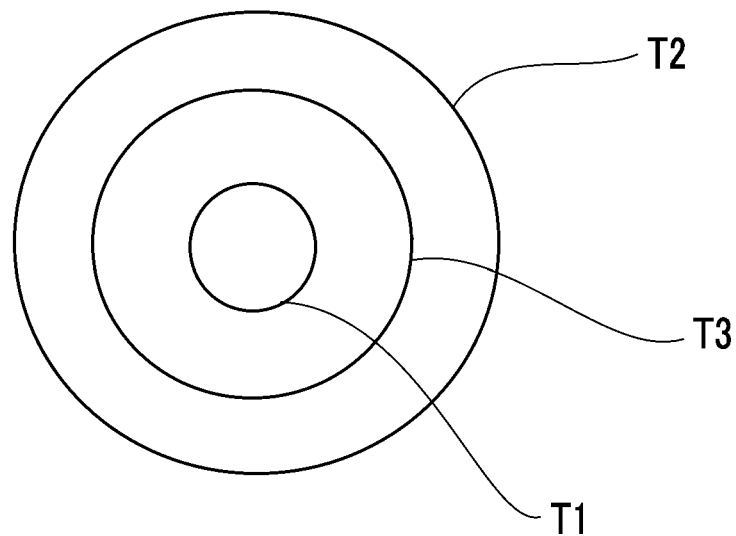
FIG. 6 is a view of the combining portion J of the three-layered tubular mixer of FIG. 5 as viewed from the O side.

FIG. 6 shows a cross section of the combining portion J in FIG. 5 as viewed from the O side. In FIG. 6, the solution of compound a1 flows in the smallest tube (T1), the solution of compound a2 flows between the smallest tube (T1) and the tube (T3) adjacent to the smallest tube (T1), and the third liquid flows between the outermost tube (T2) and the tube (T3) adjacent to the smallest tube.

The compound a1 solution and the compound a2 solution are combined by the three-layered tubular mixer (3c), and compound a1 and compound a2 are reacted while the combined liquid is flowing downstream to produce a Group III-V semiconductor nanoparticle.

In the embodiment of FIG. 4, the value (r2/r1) of the ratio of the linear velocity r2 of the solution (solution of compound a2) flowing in the flow channel adjacent to the flow channel in the smallest tube of the three-layered tubular mixer (3c) to the linear velocity r1 of the solution (solution of compound a1) flowing in the flow channel in the smallest tube of the mixer is 0.2 or less, or 5.0 or more. Thus, by providing a specific difference in the linear velocity at which both solutions flow in the mixer, the semiconductor quantum dot prepared using the obtained Group III-V semiconductor nanoparticle as a core can be made to exhibit a narrow luminescence peak half-width and sharper luminescence properties, as in the embodiment of FIG. 1. That is, it is possible to obtain a Group III-V semiconductor quantum dot with high color purity of luminescence.

In a case where the r2/r1 is set to 0.2 or less, the lower limit thereof is not particularly limited. The r2/r1 is set to usually 0.005 or more and practically 0.01 or more. In a case where the r2/r1 is set to 5.0 or more, the upper limit thereof is not particularly limited. The r2/r1 is set to usually 200 or less and practically 100 or less.

In addition, in the embodiment of FIG. 4, as described above, the third liquid is allowed to flow between the outermost tube (T2) and the tube (T3) adjacent to the smallest tube. The third liquid can prevent the reaction liquid of compound a1 and compound a2 from coming into contact with the wall surface of the flow channel, and plays a role of preventing the precipitation of particles on the wall surface of the flow channel. The third solution preferably does not substantially affect the reaction of compound a1 with compound a2. For example, the solvent described below, or a solvent containing a dispersant can be used.

In the embodiment shown in FIGS. 4 to 6, the solution of compound a1 may flow in the flow channel adjacent to the flow channel in the smallest tube, and the solution of compound a2 may flow in the flow channel in the smallest tube. Such an embodiment is also preferable as the embodiment of the production method of the present invention.

As for the method for producing a nanoparticle according to the embodiment of the present invention, as shown in FIG. 1, it is more preferred that the combining portion in a flow reaction is constituted by a two-layered tubular mixer.

In addition, it is more preferred that the r2/r1 is set to 0.2 or less.

Subsequently, the configuration of each member in the above-described embodiments and the reaction for producing a Group III-V semiconductor nanoparticle will be described in order.

[Upstream Flow Channel of Combining Region]

In the present invention, there is no particular limitation on the shape of the flow channels disposed on the upstream side of the combining region (3) (in the embodiment shown in FIGS. 1 and 4, the first flow channel (1), the second flow channel (2), and the third flow channel (10)). Usually, a tube having an equivalent diameter of about 0.1 mm to 5 cm (preferably 0.1 mm to 1 cm) and a length of about 20 cm to 50 m is used. The cross-sectional shape of the flow channel is not particularly limited, and may be a circle, an oval, or a polygon such as a rectangle or a square. It is more preferred that the cross-sectional shape of the flow channel is circular from the viewpoint of making it difficult for liquid to build up inside the tubing arrangement.

In the present specification, the "equivalent diameter" is also referred to as a corresponding (value) diameter, which is a term used in the field of mechanical engineering. In a case where an equivalent circular tube is assumed for a tubing arrangement or flow channel having a certain inner sectional shape of the tube, the inner cross-sectional diameter of the equivalent circular tube is referred to as an equivalent diameter. The equivalent diameter ($d_{eq}$) is defined as $d_{eq}=4A/p$, using A: inner cross-sectional area of tubing arrangement, and p: wetted length (inner perimeter) of tubing arrangement. In a case of being applied to a circular tube, the equivalent diameter corresponds to the inner cross-sectional diameter of the circular tube. The equivalent diameter is used for estimating flowing properties or heat transfer properties of the tubing arrangement based on the data of the equivalent circular tube, and indicates a spatial scale (representative length) of a phenomenon. The equivalent diameter of a square tube a on a side is $d_{eq}=4a^2/4a=a$. The equivalent diameter of an equilateral triangle tube a on a side is $d_{eq}=a/3^{1/2}$. In a case of a flow between parallel plates with a flow channel height of h, the equivalent diameter is $d_{eq}=2h$ (for example, refer to "Encyclopedia of Mechanical Engineering", The Japan Society of Mechanical Engineers, 1997, Maruzen Co., Ltd.).

The material of the tube constituting the flow channel is not particularly limited as long as it is a material that can withstand high temperatures at the time of nanoparticle formation, and examples thereof include stainless steel, copper (or an alloy thereof), nickel (or an alloy thereof), and titanium (or an alloy thereof). From the viewpoint of chemical resistance, the material of the tube is preferably stainless steel, a nickel alloy (hastelloy), or titanium.

[Multi-Layered Tubular Mixer]

In the present invention, a multi-layered tubular mixer is used in a combining region (3) where the solution of compound a1 and the solution of compound a2 are combined. FIGS. 1 to 6 show an embodiment using a two-layered tubular mixer (3b) and a three-layered tubular mixer (3c) as the multi-layered tubular mixer as described above. In the production method of the present invention, a multi-layered tubular mixer with four or more layers may be used in the combining region (3). As shown in FIGS. 2 and 5, the multi-layered tubular mixer is a structure comprising a tube having a multi-layered structure in which flow channels are formed in the smallest tube or between adjacent tubes, and inlets for introducing a liquid into these flow channels. In the multi-layered tubular mixer, one of the flow channel for flowing the solution of compound a1 and the flow channel for flowing the solution of compound a2 is the flow channel in the smallest tube of the multi-layered tubular mixer. The flow channel for flowing the solution of compound a1 and the flow channel for flowing the solution of compound a2 are adjacent to each other, and as described above, the ratio (r2/r1) of the linear velocity r2 of the solution flowing in the flow channel adjacent to the flow channel in the smallest tube of the multi-layered tubular mixer to the linear velocity r1 of the solution flowing in the flow channel in the smallest tube is set to 0.2 or less, or 5.0 or more.

There is no particular limitation on the material of the multi-layered tubular mixer. For example, the multi-layered tubular mixer made of a material such as stainless steel, copper (or an alloy thereof), nickel (or an alloy thereof), or titanium (or an alloy thereof) can be used.

The cross-sectional shape of the tube, flow channel, or opening of the multi-layered tubular mixer is not particularly limited and may be circular, oval, or polygonal such as rectangular or square. From the viewpoint that liquid does not easily stay in the mixer, it is more preferred that the cross-sectional shape of the tube, flow channel, or opening of the multi-layered tubular mixer is circular.

The equivalent diameter of the smallest tube (inner tube) inner diameter of the multi-layered tubular mixer is preferably 0.1 to 50 mm, more preferably 0.1 to 10 mm, and still more preferably 0.1 to 2 mm. In addition, the equivalent diameter of the outermost tube (outer tube) inner diameter is usually 0.5 to 100 mm and preferably 1 to 30 mm, although it depends on the number of layer configurations. The equivalent diameter of the inner diameter of the middle tube between the smallest tube and the outermost tube can be appropriately adjusted based on the equivalent diameters of the inner tube and the outer tube.

The multi-layered tubular mixer that can be used in the present invention can be produced by combining, for example, a joint such as Bored-Through Union Tee (manufactured by Swagelok Company) and a tubing arrangement of any inner diameter and outer shape. In addition, known structures such as the structure described in JP2006-096569A can be used as the multi-layered tubular mixer.

[Reaction Flow Channel]

The solution combined in the combining region (3) flows in the reaction flow channel (4).

The reaction flow channel (4) is preferably tubular. A tube having an equivalent diameter of about 0.1 mm to 5 cm (preferably 0.1 mm to 1 cm) and a length of about 20 cm to 50 m is usually used as the reaction flow channel (4). The cross-sectional shape of the reaction flow channel (4) is not particularly limited and may be any shape such as a circle, an oval, a rectangle, or a square. It is more preferred that the cross-sectional shape of the reaction flow channel (4) is circular from the viewpoint of making it difficult for liquid to build up inside the tubing arrangement.

The material of the tube constituting the reaction flow channel (4) is also not particularly limited, and examples thereof include stainless steel, copper (or an alloy thereof), nickel (or an alloy thereof), and titanium (or an alloy thereof). From the viewpoint of flexibility and chemical resistance, the material of the tube is preferably stainless steel, a nickel alloy (hastelloy), or titanium.

[Formation Reaction of Group III-V Semiconductor Nanoparticle]

Compound a1 and compound a2 combined in the combining region (3) react while flowing in the reaction flow channel (4) to generate crystal nuclei of the Group III-V semiconductor, and the nuclei generated in the circulation grow to produce Group III-V semiconductor nanoparticles. The Group III-V semiconductor nanoparticles produced in the reaction flow channel are usually recovered in a recovery container 7 as a dispersion liquid of Group III-V semiconductor nanoparticles by the selection of a solvent species and the action of a dispersant or the like.

One type of compound is usually used as compound a1, but two or more types of compounds may be used as compound a1. In a case where two or more types of compounds are used as compound a1, it is preferred that the Group III elements contained in each of the two or more types of compounds are the same. Similarly, one type of compound is usually used as compound a2, but two or more types of compounds may be used as compound a2. In a case where two or more types of compounds are used as compound a2, it is preferred that the Group V elements contained in each of the two or more types of compounds are the same. That is, in the production method of the present invention, it is preferred that all of the obtained Group III-V semiconductor quantum dots have the same chemical structure.

Compound a1 is a source of a cation component that constitutes a nanocrystal of a Group III-V semiconductor quantum dot. The Group III element contained in compound a1 is preferably aluminum (Al), gallium (Ga), or indium (In) and more preferably In. Compound a1 is usually a metal salt containing Al, Ga, or In.

The form of the metal salt containing Al, Ga, or In includes organic acid salts of Al, Ga, or In (for example, monocarboxylate such as acetate or propionate, hydroxycarboxylate such as glycolate or lactate, dicarboxylate such as succinate or oxalate, polycarboxylate such as citrate, aliphatic or aromatic sulfonate such as methane sulfonate or toluene sulfonate, carbonate, hydrogen carbonate, sulfamate, metal alkoxide, and metal acetylacetonate), and inorganic acid salts of Al, Ga, or In (for example, nitrate, sulfate, hydroiodide, hydrochloride, hydrobromide, hydrofluoride, perchlorate, phosphate, and hydrocyanide). In consideration of the solubility in an organic solvent, the metal salt containing Al, Ga, or In is preferably an organic acid salt.

Among the above-mentioned metal salts, preferred specific examples of the Al salt include inorganic acid salts of Al such as aluminum nitrate, aluminum sulfate, aluminum carbonate, aluminum phosphate, aluminum perchlorate, aluminum cyanide, aluminum fluoride, aluminum chloride, aluminum bromide, and aluminum iodide; and organic acid salts of Al such as aluminum acetate, aluminum oxalate, aluminum tartrate, aluminum alkoxide (for example, aluminum isopropoxide, aluminum butoxide, aluminum ethoxide, or aluminum methoxyethoxide), aluminum sulfamate, and aluminum acetylacetonate. These Al salts may be used alone or in combination thereof.

Among the above-mentioned metal salts, preferred specific examples of the Ga salt include inorganic acid salts of Ga such as gallium nitrate, gallium sulfate, gallium carbonate, gallium phosphate, gallium perchlorate, gallium cyanide, gallium fluoride, gallium chloride, gallium bromide, and gallium iodide; and organic acid salts of Ga such as gallium acetate, gallium oxalate, gallium tartrate, gallium alkoxide (for example, gallium isopropoxide, gallium butoxide, gallium ethoxide, or gallium methoxyethoxide), gallium sulfamate, and gallium acetylacetonate. These Ga salts may be used alone or in combination thereof.

Among the above-mentioned metal salts, preferred specific examples of the In salt include inorganic acid salts of In such as indium nitrate, indium sulfate, indium carbonate, indium phosphate, indium perchlorate, indium cyanide, indium fluoride, indium chloride, indium bromide, and indium iodide; and organic salts of In such as indium acetate, indium oxalate, indium tartrate, indium alkoxide (for example, indium isopropoxide, indium butoxide, indium ethoxide, or indium methoxyethoxide), indium sulfamate, and indium acetylacetonate. These metal salts may be used alone or in combination thereof.

Compound a2 is a source of an anion component that constitutes a nanocrystal of a Group III-V semiconductor quantum dot. The Group V element contained in compound a2 is preferably nitrogen (N), phosphorus (P), arsenic (As), or antimony (Sb), more preferably P or As, and still more preferably P.

In a case where compound a2 is a nitrogen-containing compound containing N, examples of the nitrogen-containing compound include ammonia, ammonium nitrosophenylhydroxylamine, ammonium fluoride, ammonium chloride, ammonium bromide, and ammonium iodide.

In a case where compound a2 is a phosphorus-containing compound containing P, examples of the phosphorus-containing compound include tris(trimethylsilyl)phosphine, tris(triethylsilyl)phosphine, tris(tri-n-propylsilyl)phosphine, tris(triisopropylsilyl)phosphine, tris(dimethylphenylsilyl)phosphine, tris(dimethylbenzylsilyl)phosphine, bis(trimethylsilyl)phosphine, tris(diethylamino)phosphine, and tris(dimethylamino)phosphine.

In a case where compound a2 is an arsenic-containing compound containing As, examples of the arsenic-containing compound include dimethylarsine, triphenylarsine, triphenoxyarsine, tris(trimethylsilyl)arsine, dimethylarsine chloride, and dimethylarsine.

In a case where compound a2 is an antimony-containing compound containing Sb, examples of the antimony-containing compound include tris(trimethylsilyl)antimony and triphenylantimony.

The solvent used for the solution of compound a1 and the solution of compound a2 is not particularly limited, and is usually an organic solvent. From the viewpoint of the dispersibility of nanoparticles to be formed or the like, it is preferable to contain a nonpolar solvent. The nonpolar solvent may be only one type or two or more types. It is preferable to use a solvent selected from alkane, alkene, benzene, and toluene as the nonpolar solvent.

It is preferred that the nonpolar solvent has a boiling point of 170° C. or higher. Preferred specific examples of such a nonpolar solvent include an aliphatic saturated hydrocarbon such as n-decane, n-dodecane, n-hexadecane, or n-octadecane; an aliphatic unsaturated hydrocarbon such as 1-undecene, 1-dodecene, 1-hexadecene, or 1-octadecene; and trioctylphosphine. Above all, the nonpolar solvent is preferably an aliphatic unsaturated hydrocarbon having 12 or more carbon atoms, and more preferably 1-octadecene. By using an organic solvent having a boiling point of 170° C. or higher, the particles are less likely to aggregate during particle formation, and therefore the solution dispersibility of the nanoparticles becomes better.

The percentage of the nonpolar solvent in the solvents is preferably 80% by volume or more, more preferably 90% by volume or more, still more preferably 95% by volume or more, and even still more preferably 99% by volume or more. It is particularly preferred that all of the solvents are nonpolar solvents.

In addition, one or two or more of the following solvents can also be used as the solvent used for each of the above-mentioned solutions.

Amide compounds such as N-methyl-2-pyrrolidone (NMP), N,N-dimethylacetamide (DMAC), and N,N-dimethylformamide; urea compounds such as N,N-dimethylethyleneurea, N,N-dimethylpropyleneurea, and tetramethylurea; lactone compounds such as γ-butyrolactone and γ-caprolactone; carbonate compounds such as propylene carbonate; ketone compounds such as methyl ethyl ketone, methyl isobutyl ketone, and cyclohexanone; ester compounds such as ethyl acetate, n-butyl acetate, butyl cellosolve acetate, butyl carbitol acetate, ethyl cellosolve acetate, and ethyl carbitol acetate; ether compounds such as diglyme, triglyme, tetraglyme, diethylene glycol, diethylene glycol ethyl methyl ether, diethylene glycol diethyl ether, diethylene glycol monomethyl ether, triethylene glycol butyl methyl ether, triethylene glycol monoethyl ether, triethylene glycol monomethyl ether, and diphenyl ether; and sulfone compounds such as sulfolane.

These solvents are preferably non-coordinating solvents. In the present specification, the "non-coordinating solvent" is a solvent having no structure capable of coordinating to a metal atom. More specifically, the non-coordinating solvent refers to a solvent having no hetero atom selected from an oxygen atom, a sulfur atom, a nitrogen atom, and a phosphorus atom in the molecule. By using a non-coordinating solvent, the particle formation reaction can be further speeded up, and nanoparticles having a more uniform composition and size distribution can be synthesized.

The water content of the solvent used in the nanoparticle formation reaction is preferably 10 ppm or less on a mass basis, from the viewpoint of preventing hydrolysis or the like of compound a2, and is usually 0 to 8 ppm. In particular, in a case where a compound having an alkylsilyl group is used as compound a2, the water content of the solvent is preferably as low as possible.

In the solution of compound a1 and the solution of compound a2, the content of the solvent is preferably 90% to 99.8% by mass and more preferably 95% to 99.5% by mass.

In the solution of compound a1 and the solution of compound a2, it is also preferable to add a compound capable of coordinating to nanoparticles produced by the reaction (hereinafter, referred to as "coordinating compound"). By carrying out the nanoparticle formation reaction in the presence of the coordinating compound, the coordinating compound can be coordinated to the surface layer of the formed nanoparticles to effectively suppress the aggregation of the particles and stabilize the dispersion state of the nanoparticles.

The coordinating compound preferably has a hydrocarbon chain having 6 or more carbon atoms and more preferably has a hydrocarbon chain having 10 or more carbon atoms, from the viewpoint of improving the dispersibility of the particles. Specific examples of such a coordinating compound include decanoic acid, lauric acid, myristic acid, palmitic acid, stearic acid, behenic acid, oleic acid, erucic acid, oleylamine, dodecylamine, dodecanethiol, 1,2-hexadecanethiol, trioctylphosphine oxide, and cetrimonium bromide.

In a case where the solution of compound a1 and the solution of compound a2 contain a coordinating compound, the content of the coordinating compound in the reaction liquid at the time of reaction initiation (in a case where the respective solutions are combined and uniformly mixed) is preferably 0.1% to 5% by mass, more preferably 0.3% to 5% by mass, still more preferably 0.5% to 5% by mass, and particularly preferably 1% to 3% by mass.

The solution of compound a1 may contain a compound containing a metal atom other than a Group III element. For example, in the synthesis of InP nanoparticles, it is known that optical properties are improved by doping Zn in an InP crystal lattice to form an In(Zn)P alloy. The Group III-V semiconductor nanoparticles in the present invention also include the form of an alloy doped with a metal atom other than a Group III element.

The reaction for forming a Group III-V semiconductor nanoparticle by combining the solution of compound a1 and the solution of compound a2 is preferably carried out at a reaction temperature of 270° C. to 350° C. In a case where compound a1 and compound a2 are mixed, the reaction occurs rapidly to form cluster nuclei of the Group III-V semiconductor. In order to grow these cluster nuclei into Group III-V semiconductor nanoparticles having a desired particle size, a high temperature reaction at 270° C. to 350° C. is required. The reason why such a high temperature reaction is required is not clear, but it is presumed that there is a thermal equilibrium with size convergence between cluster nuclei and nanoparticles. The reaction temperature of the nanoparticle formation reaction is preferably 270° C. to 320° C. and more preferably 290° C. to 310° C., from the viewpoint of further narrowing the luminescence peak half-width. In addition, by adjusting this reaction temperature, it is possible to adjust the luminescence wavelength of the quantum dot having the obtained nanoparticle as a core to some extent.

The reaction time of the above-mentioned nanoparticle formation reaction is not particularly limited as long as it can form a desired nanoparticle. From the viewpoint of making the size of the obtained nanoparticles more uniform, the reaction time of the nanoparticle formation reaction is preferably 10 seconds or more, more preferably 5 minutes or more, still more preferably 10 minutes or more, and particularly preferably 20 minutes or more. In addition, from the viewpoint of preventing aggregation of the formed nanoparticles and enhancing the uniformity of the nanoparticle size, the reaction time of the nanoparticle formation reaction is preferably 120 minutes or less, more preferably 90 minutes or less, still more preferably 60 minutes or less, even still more preferably 50 minutes or less, and particularly preferably 40 minutes or less. The reaction time is appropriately controlled by adjusting the solution sending speed, the inner diameter and length of the reaction flow channel, and the like.

In the reaction flow channel, the quantitative ratio of the Group III element to the Group V element is preferably Group III element/Group V element=1/0.1 to 1/1, more preferably 1/0.2 to 1/0.9, and still more preferably 1/0.3 to 1/0.8 (molar ratio).

In the reaction flow channel, the content of the Group III element is preferably 0.05% to 2% by mass and more preferably 0.2% to 1% by mass. In the reaction flow channel, the content of the Group V element is preferably 0.01% to 1.5% by mass and more preferably 0.05% to 0.75% by mass.

Examples of nanoparticles of Group III-V semiconductors obtained by the method for producing a nanoparticle according to the embodiment of the present invention include AlN, AlP, AlAs, AlSb, InN, InP, InAs, InSb, GaN, GaP, GaAs, and GaSb. Among them, a Group III-V semiconductor selected from InN, InP, InAs, InSb, GaN, GaP, GaAs, and GaSb is preferable; a Group III-V semiconductor selected from InN, InP, InAs, and InSb is more preferable; InP or InAs is still more preferable; and InP is particularly preferable. Each of the nanoparticles listed here is meant to include the form of the alloy described above (form having doped atoms).

[Method for Producing Group III-V Semiconductor Quantum Dot]

The method for producing a Group III-V semiconductor quantum dot according to the embodiment of the present invention (hereinafter, also referred to as the method for producing a quantum dot according to the embodiment of the present invention) includes obtaining a Group III-V semiconductor nanoparticle by the above-mentioned method for producing a nanoparticle according to the embodiment of the present invention, and introducing Ga into the surface layer of the Group III-V semiconductor nanoparticle (Ga introducing step).

In the Ga introducing step, first, the Group III-V semiconductor nanoparticles obtained by the method for producing a nanoparticle according to the embodiment of the present invention are reacted with a salt of at least one metal c1 selected from the following metal group [c] (this reaction is also referred to as "metal c1 introduction reaction"), and then the obtained particles are reacted with a salt of Ga (this reaction is also referred to as "Ga introduction reaction"). The Ga introducing step can also be carried out in a case where the Group III-V semiconductor nanoparticles obtained by the method for producing a nanoparticle according to the embodiment of the present invention contain Ga as a Group III element.

Metal Group [c]:

Ca, Sc, Ti, V, Cr, Mn, Fe, Co, Ni, Cu, and Zn

The metal c1 is one or two or more metals selected from the above metal group [c] and is preferably one metal. The metal c1 can be introduced into the surface layer of nanoparticles by the metal c1 introduction reaction. The metal c1 introduction reaction may be carried out in the presence of compound a2 described above as an anion source, or may be carried out in the absence of compound a2. In addition, compound a1 used in the nanoparticle formation reaction may coexist. Although it is not sufficiently clear how the metal c1 is introduced by the metal c1 introduction reaction, it is presumed that at least at least one of the following reactions is proceeding.

That is, in a case where the metal c1 introduction reaction is carried out in the presence of compound a2, it is considered that a crystal structure consisting of cations of metal c1 and anions grows on the surface layer of the nanoparticle, whereby the metal c1 is introduced into the surface layer of the nanoparticle; or the metal c1 is introduced into the surface layer of the nanoparticle by cation exchange between the Group III element present in the surface layer of the nanoparticles and the metal c1 or by the metal c1 being doped into the crystal lattice of the surface layer of the nanoparticles.

In a case where the metal c1 introduction reaction is carried out in the absence of compound a2, it is considered that the metal c1 is introduced into the surface layer of the nanoparticle by cation exchange between the Group III element present in the surface layer of the nanoparticles and the metal c1 or by the metal c1 being doped into the crystal lattice of the surface layer of the nanoparticles.

The metal c1 introduction reaction can be carried out by recovering the reaction liquid having passed through the reaction flow channel in a recovery container 7 in the method for producing a nanoparticle according to the embodiment of the present invention, and mixing the reaction liquid with a salt of metal c1.

In the metal c1 introduction reaction, the type of solvent that can be used in the reaction and the content of the solvent in the reaction liquid are respectively the same as the type of solvent that can be used in the above-mentioned method for producing a nanoparticle according to the embodiment of the present invention and the content of the solvent in the reaction liquid, and preferred embodiments thereof are also the same.

In addition, in a case where the metal c1 introduction reaction is carried out, the above-mentioned coordinating compound (dispersant) may be contained in the reaction liquid. In this case, the content of the coordinating compound in the reaction liquid in the metal c1 introduction reaction is preferably 0.1% to 5% by mass, more preferably 0.3% to 5% by mass, still more preferably 0.5% to 5% by mass, and particularly preferably 1% to 3% by mass.

With respect to the metal c1, it is also preferred that a salt of metal c1 and a coordinating compound are mixed in advance and heated to coordinate the coordinating compound to the metal c1, and the resulting product is added to the reaction liquid for metal c1 introduction reaction to react with the Group III-V semiconductor nanoparticles obtained by the method for producing a nanoparticle according to the embodiment of the present invention.

In the metal c1 introduction reaction, examples of the salt of metal c1 include organic acid salts of metal c1 (for example, monocarboxylate such as acetate or propionate, hydroxycarboxylate such as glycolate or lactate, dicarboxylate such as succinate or oxalate, polycarboxylate such as citrate, aliphatic or aromatic sulfonate such as methane sulfonate or toluene sulfonate, carbonate, hydrogen carbonate, sulfamate, metal alkoxide, and metal acetylacetonate), and inorganic acid salts of metal c1 (for example, nitrate, sulfate, hydroiodide, hydrochloride, hydrobromide, hydrofluoride, perchlorate, phosphate, and hydrocyanide).

In a case where the metal c1 is Ca, examples of the organic acid salt of Ca include calcium acetate, calcium propionate, calcium stearate, calcium glycolate, calcium oxalate, aliphatic or aromatic sulfonate such as calcium methanesulfonate or calcium toluenesulfonate, calcium carbonate, calcium hydrogen carbonate, calcium sulfamate, calcium ethoxide, and calcium acetylacetonate. In addition, examples of the inorganic acid salt of Ca include calcium sulfate, calcium chloride, calcium bromide, and calcium phosphate.

In a case where the metal c1 is Sc, examples of the organic acid salt of Sc include scandium acetate, scandium stearate, scandium methanesulfonate, scandium carbonate, scandium sulfamate, scandium ethoxide, and scandium acetylacetonate. In addition, examples of the inorganic acid salt of Sc include scandium nitrate, scandium chloride, scandium bromide, and scandium phosphate.

In a case where the metal c1 is Ti, examples of the organic acid salt of Ti include titanium acetate, titanium stearate, titanium glycolate, titanium oxalate, aliphatic or aromatic sulfonate such as titanium methanesulfonate or titanium toluenesulfonate, titanium carbonate, titanium isopropoxide, titanium t-butoxide, and titanium acetylacetonate. In addition, examples of the inorganic acid salt of Ti include titanium chloride.

In a case where the metal c1 is V, examples of the organic acid salt of V include vanadium acetate, vanadium stearate, vanadium carbonate, triisopropoxy vanadium oxide, and vanadium acetylacetonate. In addition, examples of the inorganic acid salt of V include vanadium oxide sulfate, vanadium chloride, vanadium bromide, and vanadium fluoride.

In a case where the metal c1 is Cr, examples of the organic acid salt of Cr include chromium acetate, chromium stearate, and chromium acetylacetonate. In addition, examples of the inorganic acid salt of Cr include chromium nitrate, chromium chloride, and chromium phosphate.

In a case where the metal c1 is Mn, examples of the organic acid salt of Mn include manganese acetate, manganese stearate, manganese 2-ethylhexanoate, manganese oxalate, manganese carbonate, manganese formate, manganese acetylacetonate, tris(2,2,6,6-tetramethyl-3,5-heptanedionato)manganese, bis(trifluoromethanesulfonyl)imide manganese, and N,N'-ethylenebis(salicylideneiminato)manganese. In addition, examples of the inorganic acid salt of Mn include manganese nitrate, manganese sulfate, manganese chloride, and manganese phosphate.

In a case where the metal c1 is Fe, examples of the organic acid salt of Fe include iron acetate, iron stearate, iron 2-ethylhexanoate, iron oxalate, iron citrate, iron methanesulfonate, iron diethyldithiocarbamate, iron methoxide, iron acetylacetonate, ferrocene, and N,N'-ethylenebis(salicylideneiminato)iron. In addition, examples of the inorganic acid salt of Fe include iron nitrate, iron sulfate, iron chloride, iron bromide, iron iodide, and iron phosphate.

In a case where the metal c1 is Co, examples of the organic acid salt of Co include cobalt acetate, cobalt stearate, cobalt oxalate, cobalt citrate, cobalt carbonate, cobalt sulfamate, tris(2,2,6,6-tetramethyl-3,5-heptanedionato)cobalt, cobalt acetylacetonate, and N,N'-ethylenebis(salicylideneiminato)cobalt. In addition, examples of the inorganic acid salt of Co include cobalt nitrate, cobalt sulfate, cobalt chloride, cobalt bromide, cobalt iodide, and cobalt phosphate.

In a case where the metal c1 is Ni, examples of the organic acid salt of Ni include nickel acetate, nickel stearate, nickel 2-ethylhexanoate, nickel lactate, aliphatic or aromatic sulfonate such as nickel trifluoromethanesulfonate or nickel toluenesulfonate, nickel carbonate, nickel 2-methoxyethoxide, nickel diethyldithiocarbamate, nickel acetylacetonate, nickel trifluoroacetylacetonate, [1,2-bis(diphenylphosphino)ethane]nickel dichloride, and N,N'-ethylenebis(salicylideneiminato)nickel. In addition, examples of the inorganic acid salt of Ni include nickel nitrate, nickel sulfate, nickel chloride, nickel bromide, and nickel iodide.

In a case where the metal c1 is Cu, examples of the organic acid salt of Cu include copper acetate, copper stearate, copper 2-ethylhexanoate, copper citrate, copper oxalate, aliphatic or aromatic sulfonate such as copper trifluoromethanesulfonate or copper toluenesulfonate, copper carbonate, copper formate, copper ethoxide, copper diethyldithiocarbamate, copper acetylacetonate, copper trifluoroacetylacetonate, bis(1,3-propanediamine)copper dichloride, bis(trifluoromethanesulfonyl)imide copper, and N,N'-ethylenebis(salicylideneiminato)copper. In addition, examples of the inorganic acid salt of Cu include copper nitrate, copper sulfate, copper chloride, copper bromide, and copper iodide.

In a case where the metal c1 is Zn, examples of the organic acid salt of Zn include zinc acetate, zinc propionate, zinc stearate, zinc laurate, zinc 2-ethylhexanoate, zinc citrate, zinc oxalate, zinc trifluoroacetate, zinc p-t-butylbenzoate, aliphatic or aromatic sulfonate such as zinc trifluoromethanesulfonate or zinc toluenesulfonate, zinc carbonate, zinc formate, zinc tert-butoxide, zinc diethyldithiocarbamate, zinc acetylacetonate, bis(2,2,6,6-tetramethyl-3,5-heptanedionato)zinc, zinc trifluoroacetylacetonate, dichloro(N,N,N',N'-tetramethylethane-1,2-diamine)zinc, bis(trifluoromethanesulfonyl)imide zinc, and N,N'-ethylenebis(salicylideneiminato)zinc. In addition, examples of the inorganic acid salt of Zn include zinc nitrate, zinc sulfate, zinc chloride, zinc bromide, zinc iodide, and zinc phosphate.

At the start of the metal c1 introduction reaction, the content of the salt of metal c1 in the reaction liquid is preferably 0.1% to 5% by mass, more preferably 0.2% to 4% by mass, and still more preferably 0.5% to 2% by mass.

In addition, at the start of the metal c1 introduction reaction, the content of the Group III-V semiconductor nanoparticles in the reaction liquid is preferably 0.05% to 5% by mass, more preferably 0.05% to 2% by mass, and still more preferably 0.1% to 2% by mass. In a case where the metal c1 is added to the reaction liquid in the state where the coordinating compound is coordinated as described above, the content of the salt of the metal c1 in the reaction liquid is a value obtained by converting the metal c1 into the state of the salt before coordinating the coordinating compound.

From the viewpoint of the reaction rate, the reaction temperature of the metal c1 introduction reaction is usually 100° C. or higher, preferably 150° C. or higher, and more preferably 180° C. or higher. In addition, from the viewpoint of solvent boiling point and operation safety, the reaction temperature of the metal c1 introduction reaction is usually 400° C. or lower, preferably 350° C. or lower, more preferably 300° C. or lower, still more preferably 250° C. or lower, and particularly preferably 230° C. or lower.

The reaction time of the metal c1 introduction reaction is appropriately adjusted depending on the purpose, and is usually 1 to 240 minutes, preferably 5 to 180 minutes, more preferably 8 to 120 minutes, and particularly preferably 10 to 60 minutes.

The Group III-V semiconductor nanoparticles obtained through the above-mentioned metal c1 introduction reaction are usually obtained in the state of a dispersion liquid, and the content of the Group III-V semiconductor nanoparticles in this dispersion liquid is preferably 0.05% to 3% by mass. The nanoparticles in the dispersion liquid are usually used in the form of a dispersion liquid without separation and recovery for the subsequent Ga introduction reaction.

In the Ga introduction reaction, the nanoparticles obtained by the metal c1 introduction reaction, in which the metal c1 has been introduced into the surface layer of the particles, are reacted with a salt of Ga. By this reaction, Ga can be introduced into the surface layer of nanoparticles obtained by the metal c1 introduction reaction, in which the metal c1 has been introduced into the surface layer of the particles. The Ga introduction reaction may be carried out in the presence of compound a2 described above as an anion source, or may be carried out in the absence of compound a2. Although it is not sufficiently clear how Ga is introduced by the Ga introduction reaction, it is presumed that at least at least one of the following reactions is proceeding.

That is, in a case where the Ga introduction reaction is carried out in the presence of compound a2, it is considered that a crystal layer or amorphous layer consisting of Ga ions and anions grows on the surface layer of the nanoparticle in which the metal c1 has been introduced into the surface layer of the particle, whereby Ga is introduced into the surface layer of nanoparticles, or separately from this reaction, Ga is also introduced into the surface layer of nanoparticles by cation exchange between the metal c1 present in the surface layer of nanoparticles and Ga.

In addition, in a case where the Ga introduction reaction is carried out in the absence of compound a2, it is considered that Ga is introduced into the surface layer of nanoparticles by cation exchange between the metal c1 present in the surface layer of nanoparticles and Ga.

The Ga introduction reaction may be carried out by mixing a salt of Ga into the reaction liquid of the metal c1 introduction reaction after the metal c1 introduction reaction. In addition, the Ga introduction reaction may be carried out in such a manner that, after completion of the metal c1 introduction reaction, the obtained nanoparticles, in which the metal c1 has been introduced into the surface layer of the particles, are re-dispersed in another solvent, and then the re-dispersion liquid and a salt of Ga are mixed.

In the Ga introduction reaction, the type of solvent that can be used in the reaction and the content of the solvent in the reaction liquid are respectively the same as the type of solvent that can be used in the above-mentioned nanoparticle formation reaction and the content of the solvent in the reaction liquid, and preferred embodiments thereof are also the same.

In addition, in a case where the Ga introduction reaction is carried out, the above-mentioned coordinating compound may be contained in the reaction liquid. In this case, the content of the coordinating compound in the reaction liquid in the Ga introduction reaction is preferably 0.1% to 5% by mass, more preferably 0.3% to 5% by mass, still more preferably 0.5% to 5% by mass, and particularly preferably 1% to 3% by mass.

With respect to Ga, it is also preferred that a salt of Ga and a coordinating compound are mixed in advance and heated to coordinate the coordinating compound to Ga, and the resulting product is added to the reaction liquid for Ga introduction reaction, followed by reaction with the nanoparticles obtained by the metal c1 introduction reaction, in which the metal c1 has been introduced into the surface layer of the particles.

In the Ga introduction reaction, examples of the salt of Ga to be used include organic acid salts of Ga (for example, monocarboxylate such as acetate or propionate, hydroxycarboxylate such as glycolate or lactate, dicarboxylate such as succinate or oxalate, polycarboxylate such as citrate, aliphatic or aromatic sulfonate such as methane sulfonate or toluene sulfonate, carbonate, hydrogen carbonate, sulfamate, metal alkoxide, and metal acetylacetonate), and inorganic acid salts of Ga (for example, nitrate, sulfate, hydroiodide, hydrochloride, hydrobromide, hydrofluoride, perchlorate, phosphate, and hydrocyanide).

Examples of the organic acid salt of Ga include gallium acetate, gallium stearate, gallium 2-ethylhexanoate, aliphatic or aromatic sulfonate such as gallium trifluoromethanesulfonate or gallium toluenesulfonate, gallium ethoxide, gallium isopropoxide, gallium acetylacetonate, and gallium trifluoroacetylacetonate. In addition, examples of the inorganic acid salt of Ga include gallium nitrate, gallium sulfate, gallium chloride, gallium bromide, gallium iodide, and gallium phosphate.

At the start of the Ga introduction reaction, the content of the salt of Ga in the reaction liquid is preferably 0.1% to 5% by mass, more preferably 0.2% to 4% by mass, and still more preferably 0.5% to 2% by mass.

In addition, at the start of the Ga introduction reaction, the content of the nanoparticles in which the metal c1 has been introduced into the surface layer of the particles, in the reaction liquid, is preferably 0.05% to 5% by mass, more preferably 0.05% to 2% by mass, and still more preferably 0.1% to 2% by mass. In a case where Ga is added to the reaction liquid in the state where the coordinating compound is coordinated as described above, the content of the salt of Ga in the reaction liquid is a value obtained by converting Ga into the state of the salt before coordinating the coordinating compound.

The reaction temperature of the Ga introduction reaction is usually 100° C. or higher, preferably 150° C. or higher, and more preferably 180° C. or higher. In addition, the reaction temperature of the Ga introduction reaction is usually 400° C. or lower, preferably 350° C. or lower, more preferably 300° C. or lower, still more preferably 250° C. or lower, and even still more preferably 220° C. or lower.

The reaction time of the Ga introduction reaction is appropriately adjusted depending on the purpose, and is usually 1 to 240 minutes, preferably 10 to 180 minutes, more preferably 15 to 120 minutes, and particularly preferably 20 to 90 minutes.

The Group III-V semiconductor nanoparticles obtained through the above-mentioned Ga introduction reaction are usually obtained in the state of a dispersion liquid, and the content of Group III-V semiconductor nanoparticles in this dispersion liquid is preferably 0.05% to 3% by mass. The nanoparticles in the dispersion liquid are usually used in the form of a dispersion liquid without separation and recovery for the intended reaction or application.

It is also preferred that the method for producing a semiconductor quantum dot according to the embodiment of the present invention includes a step of forming a shell layer on the surface of nanoparticles into which Ga has been introduced after the Ga introduction reaction. The shell layer can adopt a shell layer in a form that can be usually adopted as a shell layer of quantum dots, and a preferred example thereof may be a shell layer formed of ZnS, ZnO, ZnSe, $ZnSe_xS_{1-x}$ (0<X<1), ZnTe, $In_2O_3$, or CuO.

The shell layer can be formed by a conventional method, and for example, reference can be made to the description of JP2012-525467A, JP2015-529698A, JP2014-523634A, JP2015-127362A, Japanese Patent No. 4565152, Japanese Patent No. 4344613, U.S. Pat. Nos. 7,105,051, 8,481,112, APPLIED PHYSICS LETTERS, 2010, Vol. 97, p. 193104, and ACS Appl. Mater. Interfaces, 2014, Vol. 6, pp. 18233 to 18242.

For example, the shell layer of ZnS can be formed by adding an acetate of Zn and 1-dodecanethiol and, if necessary, a coordinating compound to the reaction liquid after the Ga introduction reaction, followed by reaction, for example, at a temperature of 200° C. or higher for several hours. Other shell layers can also be formed in accordance with this method by changing the raw materials used according to the purpose. In addition, the shell layer can also be formed by a reaction under high temperature conditions using an organic metal such as dimethylzinc or diethylzinc as a source of Zn, or a thermal decomposition reaction of zinc dialkyldithiocarbamate.

The shell layer is preferably ZnS, ZnO, ZnSe, or $ZnSe_xS_{1-x}$ and more preferably ZnS.

The Group III-V semiconductor quantum dots obtained by the production method of the present invention preferably have an average particle size of 1 to 10 nm and more preferably 1 to 6 nm, in a form in which the shell layer is not provided. In a case where the Group III-V semiconductor quantum dots obtained by the production method of the present invention have a form having a shell layer, the average particle size of the quantum dots including the shell layer is preferably 2 to 10 nm and more preferably 2 to 8 nm.

[Flow Reaction System]

The flow reaction system according to the embodiment of the present invention is a system suitable for carrying out the method for producing a nanoparticle according to the embodiment of the present invention described above.

That is, the flow reaction system according to the embodiment of the present invention is a flow reaction system for producing a Group III-V semiconductor nanoparticle, including a first flow channel through which a solution of compound a1 containing a Group III element flows, a second flow channel through which a solution of compound a2 containing a Group V element flows, a combining portion where the first flow channel and the second flow channel are combined, and a reaction flow channel connected to the downstream of the combining portion, in which the combining portion is constituted by a multi-layered tubular mixer. A preferred embodiment of this system is shown in FIGS. 1 and 4, and the configuration of each member is as described in the method for producing a nanoparticle according to the embodiment of the present invention described above.

The present invention will be described in more detail based on the following Examples, but the present invention is not limited thereto.

EXAMPLES

[Preparation of Compound a1 Solution-1]

In a glove box filled with dry argon, 1-octadecene (91 ml), indium acetate (980 mg), and palmitic acid (2.546 g) were added to a 300 ml eggplant flask which was then subjected to vacuum degassing at 130° C. for 30 minutes. The 1-octadecene used in this example was 1-octadecene subjected to distillation under reduced pressure with calcium hydride and having a water content of 6 ppm as calculated by Karl Fischer method. The resulting solution is referred to as "In solution".

[Preparation of Compound a1 Solution-2]

In a glove box filled with dry argon, 1-octadecene (90 ml), indium acetate (700 mg), zinc acetate (240 mg), and palmitic acid (2.425 g) were added to a 300 ml eggplant flask which was then subjected to vacuum degassing at 130° C. for 10 minutes. Next, the flask was filled with dry argon and brought to atmospheric pressure, followed by heating at 200° C. for 30 minutes to dissolve zinc acetate, cooling again to 130° C., and vacuum degassing for 30 minutes. As 1-octadecene, one having a water content of 6 ppm was used as described above. The resulting solution is referred to as "Zn-containing In solution".

[Preparation of Compound a2 Solution]

In a glove box filled with dry argon, tris(trimethylsilyl)phosphine (hereinafter, referred to as "P(TMS)$_3$") and 1-octadecene were added to a 200 ml eggplant flask to prepare 100 ml of a solution containing P(TMS)$_3$ at a predetermined concentration described later. The resulting solution is referred to as "P solution".

[Preparation of Metal c1 Solution]

In a glove box filled with dry argon, 1-octadecene (50 ml), zinc acetate (220 mg), and 2-ethylhexanoic acid (346 mg) were added to a 100 ml eggplant flask which was then subjected to vacuum degassing at 130° C. for 10 minutes. Next, the flask was filled with dry argon and brought to atmospheric pressure, followed by heating at 200° C. for 30 minutes, cooling again to 130° C., and vacuum degassing for 30 minutes. As 1-octadecene, one having a water content of 6 ppm was used as described above. The resulting solution is referred to as "Zn solution".

[Preparation of Ga Solution]

In a glove box filled with dry argon, a 1-octadecene (80 ml), gallium chloride (300 mg), and oleic acid (1.88 ml) were taken in a 100 ml small glass bottle and heated and mixed for approximately 15 minutes on a 90° C. hot plate placed in the glove box, until the gallium chloride was dissolved. As 1-octadecene, a reagent having a water content of 15 ppm or more and less than 25 ppm was used as it was. The resulting solution is referred to as "Ga solution".

[Preparation of Group III-V Semiconductor Quantum Dots]

Figures 8, 9:
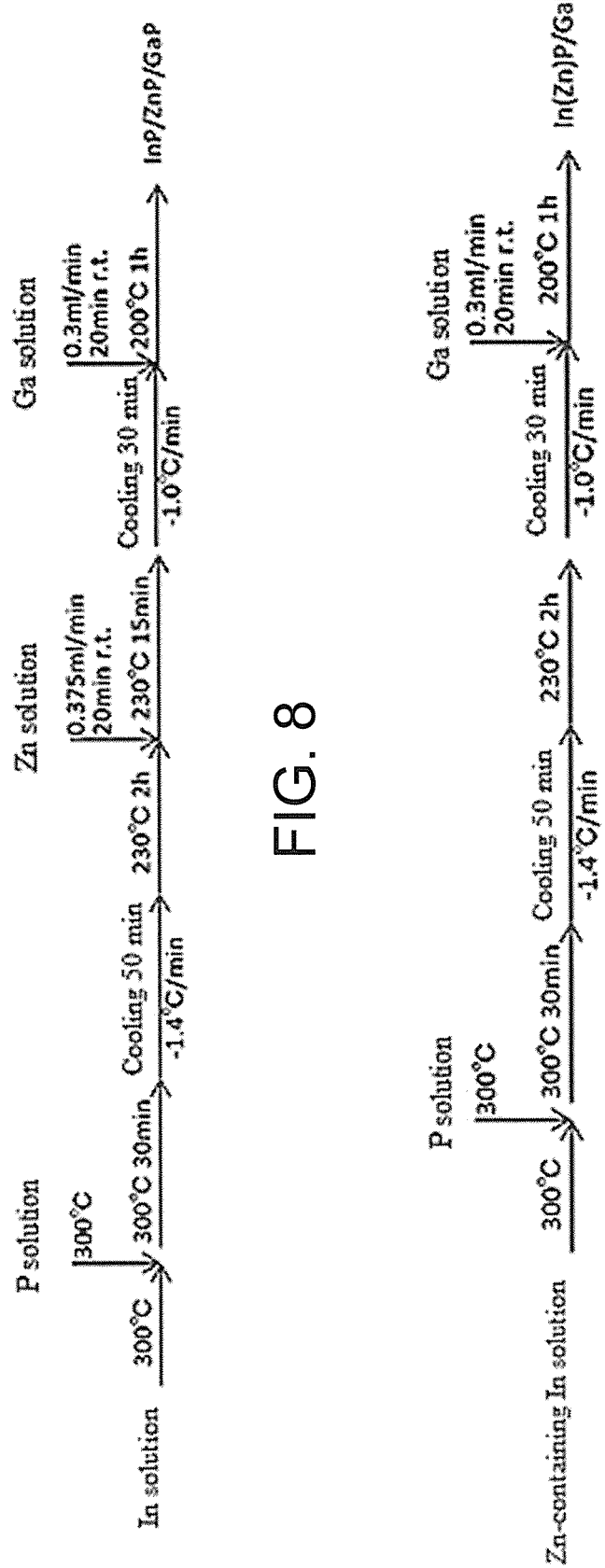
FIG. 8 shows a reaction scheme of a flow reaction system adopted in the Examples to prepare InP nanoparticles.
FIG. 9 shows a preparation flow of a flow reaction system adopted in the Examples to prepare In(Zn)P nanoparticles.

InP nanoparticles were prepared using a flow reaction system described later according to the reaction scheme shown in FIG. 8, and InP quantum dots having Ga introduced into the surface layer thereof (InP/ZnP/GaP) were prepared using the InP nanoparticles as a core.

In addition, In(Zn)P nanoparticles were prepared using a flow reaction system described later according to the preparation flow shown in FIG. 9, and In(Zn)P quantum dots having Ga introduced into the surface layer thereof (In(Zn)P/GaP) were prepared using the In(Zn)P nanoparticles as a core.

<Flow Reaction System>

Figure 7:
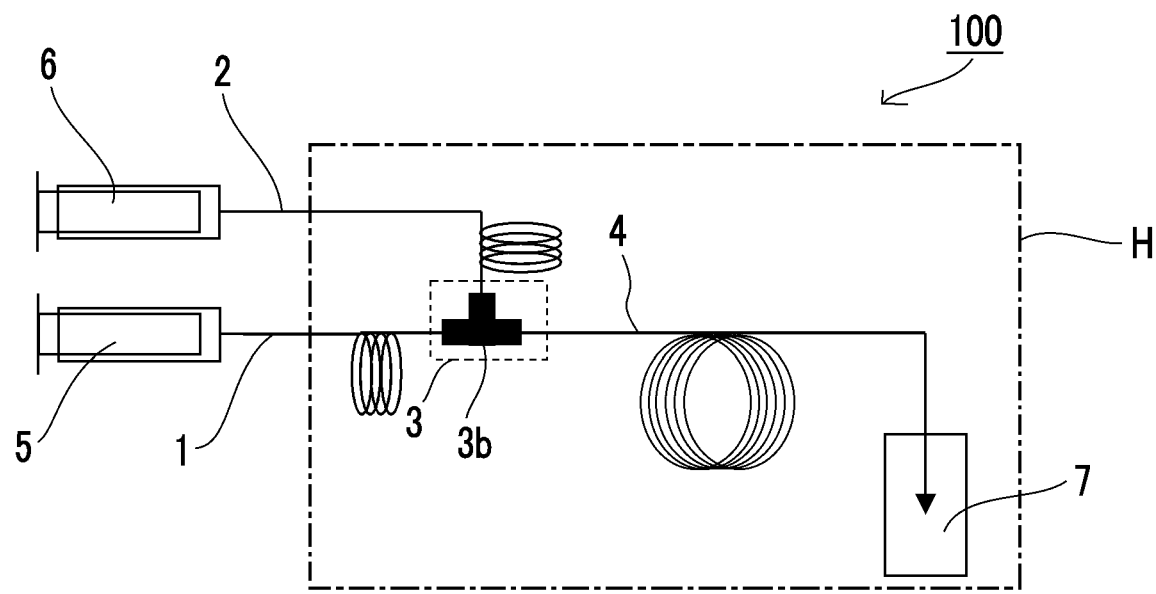
FIG. 7 is a view showing the flow reaction system adopted in the Examples.

The flow reaction system shown in FIG. 7 was adopted. All tubing arrangements and mixers were made of SUS316.

—Solution Introduction Portion—

As a means for introducing the In solution and the Zn-containing In solution, a syringe with a volume of 100 ml and made of SUS316 attached to a syringe pump (PHD ULTRA manufactured by Harvard Apparatus, Inc.) was used. The tip of the syringe was connected to a tubing arrangement having an outer diameter of 1/16 inch and an inner diameter of 1 mm, and this tubing arrangement was introduced into an electric furnace (H) set at 300° C. A pressure gauge (not shown) was installed in the tubing arrangement up to the electric furnace, and the temperature was maintained at 150° C. with a ribbon heater including the pressure gauge from the tip of the syringe to the electric furnace. In order to raise the temperature of the liquid to be flowed to the set temperature (300° C.) of the electric furnace, the electric furnace was provided with a preheating tubing arrangement wound in a coil shape and having an outer diameter of 1/16 inch, an inner diameter of 1 mm, and a length of 5 m, and the downstream portion of the preheating tubing arrangement was connected to a two-layered tubular mixer in the electric furnace.

In addition, as a means for introducing the P solution, a syringe with a volume of 100 ml and made of glass attached to a syringe pump (PHD ULTRA manufactured by Harvard Apparatus, Inc.) was used. The tip of the syringe was connected to a tubing arrangement having an outer diameter of 1/16 inch and an inner diameter of 1 mm, and this tubing arrangement was introduced into an electric furnace (H) set at 300° C. A pressure sensor was installed in the tubing arrangement up to the electric furnace. In order to raise the temperature of the liquid to be flowed to the set temperature (300° C.) of the electric furnace, the electric furnace was provided with a preheating tubing arrangement wound in a coil shape and having an outer diameter of 1/16 inch, an inner diameter of 1 mm, and a length of 6 m, and the downstream portion of the preheating tubing arrangement was connected to a mixer in the electric furnace.

—Two-Layered Tubular Mixer, Reaction Flow Channel, and Flask—

As a mixer for combining the In solution or the Zn-containing In solution and the P solution, a concentric cylindrical two-layered tubular mixer shown in FIGS. 2 and 3 was used. A tubing arrangement with an outer tube outer diameter of 1/8 inch, an outer tube inner diameter of 2.17 mm, and an inner tube outer diameter of 1/16 inch was used for the flow channel in this mixer, and the inner tube inner diameter was either 0.8 mm, 0.5 mm, or 0.25 mm.

The liquid that has flowed out of the mixer was allowed to flow through the inside of the tubing arrangement wound in the form of a coil and having an outer diameter of 1/8 inch, an inner diameter of 2.17 mm, and a length of 10.5 m to reach the outlet of the electric furnace. The reaction liquid leaving the electric furnace was introduced into a flask placed in an oil bath at 300° C. The flask used was filled with dry argon in advance.

It was configured so that the P solution was introduced into a flow channel flowing inside the outer tube and outside the inner tube of the two-layered tubular mixer (a flow channel between the smallest tube and a tube adjacent to the smallest tube, which is hereinafter referred to as "outer flow channel"); the In solution or Zn-containing In solution was allowed to flow into a flow channel flowing inside the inner tube (smallest tube) (hereinafter, referred to as "inner flow channel"); and both solutions were combined so as to flow in a parallel direction at the downstream end of the inner tube. As will be described later, in Example 2-1, the In solution was allowed to flow through the outer flow channel, and the P solution was allowed to flow through the inner flow channel.

[Analysis Method]

<Average Particle Size>

In the present invention, the average particle size of the particles is a value measured by a transmission electron microscope. More specifically, for 100 particles randomly selected by a high resolution transmission electron microscope (HR-TEM), the occupied area of particles is determined by an image processing device from the projected area. The total occupied area of 100 particles is divided by the number (100) of the selected particles. Then, the average particle size is calculated as the average value of the diameters of the circles (average equivalent circle diameter) corresponding to the obtained values. The average particle size does not include the particle size of secondary particles formed by aggregation of primary particles.

<Luminescence Peak Half-Width>

1 ml of a dispersion liquid of semiconductor quantum dots was dispersed in 4 ml of toluene, and the fluorescence maximum wavelength and the fluorescence peak half-width were measured using a fluorescence spectrophotometer (F-7000, manufactured by Hitachi High-Tech Science Corporation, excitation wavelength: 450 nm).

[Example 1-1] Preparation of InP Nanoparticles

InP nanoparticles were prepared as follows using the flow reaction system of FIG. 7 described above.

An In solution and a P solution (P(TMS)$_3$ concentration: 23.1 mmol/L) were filled in a syringe, and each solution was sent at 20 ml/min. The mixer used was a two-layered tubular mixer with an inner tube inner diameter of 0.5 mm, in which the P solution was flowed to the outer flow channel of this mixer and the In solution was flowed to the inner flow channel. The value (r2/r1) of the ratio of the linear velocity (r2) of the solution flowing in the outer flow channel to the linear velocity (r1) of the liquid flowing in the inner flow channel in the mixer was 0.125. The reaction liquid discharged from the mixer was allowed to flow for about 30 seconds through a tubing arrangement having an outer diameter of ⅛ inch, an inner diameter of 2.17 mm, and a length of 10.5 m from the outlet of the mixer to the outlet of the electric furnace, and was then received in a flask heated to 300° C. installed at the outlet of the electric furnace. Thus, a dispersion liquid of InP nanoparticles was obtained in the flask.

[Example 1-2] Preparation of InP Quantum Dots 19.5 ml of the InP nanoparticle dispersion liquid collected in the 300° C. flask was kept at 300° C. for 30 minutes, cooled to 230° C. at a constant falling rate over 50 minutes, and further kept at 230° C. for 2 hours. Thereafter, the Zn solution was added thereto at a constant rate of 0.375 ml per minute for 20 minutes (7.5 ml in total) using a syringe pump, followed by keeping at 230° C. for additional 15 minutes, and then cooling to 200° C. over 30 minutes. Thereafter, the Ga solution was added thereto at a constant rate of 0.30 ml per minute for 20 minutes (6 ml in total) using a syringe pump, followed by further keeping at 200° C. for 1 hour to obtain InP quantum dots. The elemental composition in this dispersion liquid was In/Zn/P/Ga=1/0.5/0.625/0.375 (molar ratio), and the content of InP quantum dots in the dispersion liquid was 0.4% by mass.

The obtained InP quantum dots had an average particle size of 3 nm, a fluorescence peak wavelength of 542 nm, and a half-width of 35 nm.

[Example 2-1] Preparation of InP Nanoparticles

A dispersion liquid of InP nanoparticles was obtained in a flask in the same manner as in Example 1-1, except that, in Example 1-1, the In solution was allowed to flow in the outer flow channel of the two-layered tubular mixer and the P solution was allowed to flow in the inner flow channel.

[Example 2-2] Preparation of InP Quantum Dots

An InP quantum dot dispersion liquid containing 0.4% by mass of InP quantum dots was obtained in the same manner as in Example 1-2, except that 19.5 ml of the InP nanoparticle dispersion liquid obtained in the flask in Example 2-1 was used in place of 19.5 ml of the InP nanoparticle dispersion liquid obtained in the flask in Example 1-1. The elemental composition in this dispersion liquid was In/Zn/P/Ga=1/0.5/0.625/0.375 (molar ratio).

The obtained InP quantum dots had an average particle size of 3 nm, a fluorescence peak wavelength of 544 nm, and a half-width of 37 nm.

[Example 3-1] Preparation of InP Nanoparticles

A dispersion liquid of InP nanoparticles was obtained in a flask in the same manner as in Example 1-1, except that, in Example 1-1, the inner diameter of the smallest tube (inner tube) of the two-layered tubular mixer was 0.25 mm. In this example, the value (r2/r1) of the ratio of the linear velocity (r2) of the solution flowing in the outer flow channel to the linear velocity (r1) of the liquid flowing in the inner flow channel in the mixer was 0.03.

[Example 3-2] Preparation of InP Quantum Dots

An InP quantum dot dispersion liquid containing 0.4% by mass of InP quantum dots was obtained in the same manner as in Example 1-2, except that 19.5 ml of the InP nanoparticle dispersion liquid obtained in the flask in Example 3-1 was used in place of 19.5 ml of the InP nanoparticle dispersion liquid obtained in the flask in Example 1-1. The elemental composition in this dispersion liquid was In/Zn/P/Ga=1/0.5/0.625/0.375 (molar ratio).

The obtained InP quantum dots had an average particle size of 3 nm, a fluorescence peak wavelength of 548 nm, and a half-width of 32 nm.

[Example 4-1] Preparation of InP Nanoparticles

A dispersion liquid of InP nanoparticles was obtained in a flask in the same manner as in Example 3-1, except that, in Example 3-1, the concentration of P(TMS)$_3$ in the P solution was changed to 13.8 mmol/L.

[Example 4-2] Preparation of InP Quantum Dots

An InP quantum dot dispersion liquid containing 0.3% by mass of InP quantum dots was obtained in the same manner as in Example 3-2, except that 19.5 ml of the InP nanoparticle dispersion liquid obtained in the flask in Example 4-1 was used in place of 19.5 ml of the InP nanoparticle dispersion liquid obtained in the flask in Example 3-1. The elemental composition in this dispersion liquid was In/Zn/P/Ga=1/0.5/0.375/0.375 (molar ratio).

The obtained InP quantum dots had an average particle size of 3 nm, a fluorescence peak wavelength of 570 nm, and a half-width of 48 nm.

[Example 5-1] Preparation of InP Nanoparticles

A dispersion liquid of InP nanoparticles was obtained in a flask in the same manner as in Example 3-1, except that, in Example 3-1, the concentration of $P(TMS)_3$ in the P solution was changed to 18.5 mmol/L.

[Example 5-2] Preparation of InP Quantum Dots

An InP quantum dot dispersion liquid containing 0.4% by mass of InP quantum dots was obtained in the same manner as in Example 3-2, except that 19.5 ml of the InP nanoparticle dispersion liquid obtained in the flask in Example 5-1 was used in place of 19.5 ml of the InP nanoparticle dispersion liquid obtained in the flask in Example 3-1. The elemental composition in this dispersion liquid was In/Zn/P/Ga=1/0.5/0.5/0.375 (molar ratio).

The obtained InP quantum dots had an average particle size of 3 nm, a fluorescence peak wavelength of 565 nm, and a half-width of 41 nm.

[Example 6-1] Preparation of InP Nanoparticles

A dispersion liquid of InP nanoparticles was obtained in a flask in the same manner as in Example 3-1, except that, in Example 3-1, the concentration of $P(TMS)_3$ in the P solution was changed to 27.7 mmol/L.

[Example 6-2] Preparation of InP Quantum Dots

An InP quantum dot dispersion liquid containing 0.5% by mass of InP quantum dots was obtained in the same manner as in Example 3-2, except that 19.5 ml of the InP nanoparticle dispersion liquid obtained in the flask in Example 6-1 was used in place of 19.5 ml of the InP nanoparticle dispersion liquid obtained in the flask in Example 3-1. The elemental composition in this dispersion liquid was In/Zn/P/Ga=1/0.5/0.75/0.375 (molar ratio).

The obtained InP quantum dots had an average particle size of 3 nm, a fluorescence peak wavelength of 552 nm, and a half-width of 45 nm.

[Example 7-1] Preparation of in(Zn)P Nanoparticles

In(Zn)P nanoparticles were prepared as follows using the flow reaction system of FIG. 7 described above.

A Zn-containing In solution and a P solution ($P(TMS)_3$ concentration: 20.0 mmol/L) were filled in a syringe, and each solution was sent at 20 ml/min. The mixer used was a two-layered tubular mixer with an inner tube inner diameter of 0.25 mm, in which the P solution was flowed to the outer flow channel of this mixer and the Zn-containing In solution was flowed to the inner flow channel. The value (r2/r1) of the ratio of the linear velocity (r2) of the solution flowing in the outer flow channel to the linear velocity (r1) of the liquid flowing in the inner flow channel in the mixer was 0.03. The reaction liquid discharged from the mixer was allowed to flow for about 30 seconds through a tubing arrangement having an outer diameter of ⅛ inch, an inner diameter of 2.17 mm, and a length of 10.5 m from the outlet of the mixer to the outlet of the electric furnace, and was then received in a flask heated to 300° C. installed at the outlet of the electric furnace. Thus, a dispersion liquid of In(Zn)P nanoparticles was obtained in the flask.

[Example 7-2] Preparation of in(Zn)P Quantum Dots 27 ml of the In(Zn)P nanoparticle dispersion liquid collected in the 300° C. flask was kept at 300° C. for 30 minutes, cooled to 230° C. at a constant falling rate over 50 minutes, and further kept at 230° C. for 2 hours. Thereafter, the dispersion liquid was cooled to 200° C. over 30 minutes, and the Ga solution was added thereto at a constant rate of 0.30 ml per minute for 20 minutes (6 ml in total) using a syringe pump, followed by further keeping at 200° C. for 1 hour to obtain In(Zn)P quantum dots. The elemental composition in this dispersion liquid was In/Zn/P/Ga=1/0.5/0.625/0.375 (molar ratio). The content of In(Zn)P quantum dots in the dispersion liquid was 0.4% by mass.

The obtained In(Zn)P quantum dots had an average particle size of 3 nm, a fluorescence peak wavelength of 500 nm, and a half-width of 39 nm.

[Comparative Example 1-1] Preparation of InP Nanoparticles

A dispersion liquid of InP nanoparticles was obtained in a flask in the same manner as in Example 4-1, except that, in Example 4-1, the flow rates of the In solution and P solution sent from the syringe were 5 ml/min, a T-shaped mixer with an inner diameter of 0.5 mm was used in place of the two-layered tubular mixer, and the reaction liquid discharged from the mixer was allowed to flow through a tubing arrangement having an outer diameter of 1/16 inch, an inner diameter of 1 mm, and a length of 6 m from the outlet of the mixer to the outlet of the electric furnace. In a case where the T-shaped mixer was used and then in a case where the flow rate was increased to more than 5 ml/min, aggregates were deposited in the mixer and at the outlet of the mixer, and therefore the pressure of the liquid sending was significantly increased.

The T-shaped mixer was connected such that the In solution and the P solution of the three channels were in head-on collision with each other, and the collided mixed liquid was allowed to flow to the reaction flow channel through the side flow channels.

[Comparative Example 1-2] Preparation of InP Quantum Dots

An InP quantum dot dispersion liquid containing 0.3% by mass of InP quantum dots was obtained in the same manner as in Example 4-2, except that, in Example 4-2, 19.5 ml of the InP nanoparticle dispersion liquid obtained in the flask in Comparative Example 1-1 was used in place of 19.5 ml of the InP nanoparticle dispersion liquid obtained in the flask in Example 4-1. The elemental composition in this dispersion liquid was In/Zn/P/Ga=1/0.5/0.375/0.375 (molar ratio).

The obtained InP quantum dots had an average particle size of 3 nm, a fluorescence peak wavelength of 573 nm, and a half-width of 50 nm.

[Comparative Example 2-1] Preparation of InP Nanoparticles

A dispersion liquid of InP nanoparticles was obtained in the same manner as in Comparative Example 1-1, except that, in Comparative Example 1-1, the concentration of P(TMS)$_3$ in the P solution was changed to 18.5 mmol/L.

[Comparative Example 2-2] Preparation of InP Quantum Dots

An InP quantum dot dispersion liquid containing 0.4% by mass of InP quantum dots was obtained in the same manner as in Comparative Example 1-2, except that, in Comparative Example 1-2, 19.5 ml of the InP nanoparticle dispersion liquid obtained in the flask in Comparative Example 2-1 was used in place of 19.5 ml of the InP nanoparticle dispersion liquid obtained in the flask in Comparative Example 1-1. The elemental composition in this dispersion liquid was In/Zn/P/Ga=1/0.5/0.5/0.375 (molar ratio).

The obtained InP quantum dots had an average particle size of 3 nm, a fluorescence peak wavelength of 570 nm, and a half-width of 43 nm.

[Comparative Example 3-1] Preparation of InP Nanoparticles

A dispersion liquid of InP nanoparticles was obtained in the same manner as in Comparative Example 1-1, except that, in Comparative Example 1-1, the concentration of P(TMS)$_3$ in the P solution was changed to 23.1 mmol/L.

[Comparative Example 3-2] Preparation of InP Quantum Dots

An InP quantum dot dispersion liquid containing 0.4% by mass of InP quantum dots was obtained in the same manner as in Comparative Example 1-2, except that, in Comparative Example 1-2, 19.5 ml of the InP nanoparticle dispersion liquid obtained in the flask in Comparative Example 3-1 was used in place of 19.5 ml of the InP nanoparticle dispersion liquid obtained in the flask in Comparative Example 1-1. The elemental composition in this dispersion liquid was In/Zn/P/Ga=1/0.5/0.625/0.375 (molar ratio).

The obtained InP quantum dots had an average particle size of 3 nm, a fluorescence peak wavelength of 550 nm, and a half-width of 39 nm.

[Comparative Example 4-1] Preparation of InP Nanoparticles

A dispersion liquid of InP nanoparticles was obtained in the same manner as in Comparative Example 1-1, except that, in Comparative Example 1-1, the concentration of P(TMS)$_3$ in the P solution was changed to 27.7 mmol/L.

[Comparative Example 4-2] Preparation of InP Quantum Dots

An InP quantum dot dispersion liquid containing 0.5% by mass of InP quantum dots was obtained in the same manner as in Comparative Example 1-2, except that, in Comparative Example 1-2, 19.5 ml of the InP nanoparticle dispersion liquid obtained in the flask in Comparative Example 4-1 was used in place of 19.5 ml of the InP nanoparticle dispersion liquid obtained in the flask in Comparative Example 1-1. The elemental composition in this dispersion liquid was In/Zn/P/Ga=1/0.5/0.75/0.375 (molar ratio).

The obtained InP quantum dots had an average particle size of 3 nm, a fluorescence peak wavelength of 546 nm, and a half-width of 50 nm.

[Comparative Example 5-1] Preparation of InP Nanoparticles

A dispersion liquid of InP nanoparticles was obtained in the same manner as in Example 1-1, except that, in Example 1-1, the inner diameter of the smallest tube of the two-layered tubular mixer was 0.8 mm. The value (r2/r1) of the ratio of the linear velocity (r2) of the solution flowing in the outer flow channel to the linear velocity (r1) of the solution flowing in the inner flow channel in the mixer was 0.3.

[Comparative Example 5-2] Preparation of InP Quantum Dots

An InP quantum dot dispersion liquid containing 0.4% by mass of InP quantum dots was obtained in the same manner as in Example 1-2, except that, in Example 1-2, 19.5 ml of the InP nanoparticle dispersion liquid obtained in the flask in Comparative Example 5-1 was used in place of 19.5 ml of the InP nanoparticle dispersion liquid obtained in the flask in Example 1-1. The elemental composition in this dispersion liquid was In/Zn/P/Ga=1/0.5/0.625/0.375 (molar ratio).

The obtained InP quantum dots had an average particle size of 3 nm, a fluorescence peak wavelength of 510 nm, and a half-width of 69 nm.

[Comparative Example 6-1] Preparation of in(Zn)P Nanoparticles

A dispersion liquid of InP nanoparticles was obtained in a flask in the same manner as in Example 7-1, except that, in Example 7-1, the flow rates of the Zn-containing In solution and P solution sent from the syringe were 5 ml/min, a T-shaped mixer with an inner diameter of 0.5 mm was used in place of the two-layered tubular mixer, and the reaction liquid discharged from the mixer was allowed to flow through a tubing arrangement having an outer diameter of $\frac{1}{16}$ inch, an inner diameter of 1 mm, and a length of 6 m from the outlet of the mixer to the outlet of the electric furnace.

The T-shaped mixer was connected such that the Zn-containing In solution and the P solution of the three channels were in head-on collision with each other, and the collided mixed liquid was allowed to flow to the reaction flow channel through the side flow channels.

[Comparative Example 6-2] Preparation of in(Zn)P Quantum Dots

An InP quantum dot dispersion liquid containing 0.4% by mass of In(Zn)P quantum dots was obtained in the same manner as in Example 7-2, except that, in Example 7-2, 27 ml of the In(Zn)P nanoparticle dispersion liquid obtained in the flask in Comparative Example 6-1 was used in place of 27 ml of the In(Zn)P nanoparticle dispersion liquid obtained in the flask in Example 7-1. The elemental composition in this dispersion liquid was In/Zn/P/Ga=1/0.5/0.625/0.375 (molar ratio).

The obtained In(Zn)P quantum dots had an average particle size of 3 nm, a fluorescence peak wavelength of 505 nm, and a half-width of 47 nm.

The results of each of the above Examples and Comparative Examples are summarized in Table 1 below.

TABLE 1

| | Mixer constituting combining portion | Core nanoparticles | In/Zn/P/Ga ratio (molar ratio) in quantum dot dispersion liquid | Linear velocity ratio in mixer (r2/r1) | Luminescence peak wavelength (nm) | Luminescence peak half-width (nm) |
|---|---|---|---|---|---|---|
| Example 1 | Two-layered tubular | InP | 1/0.5/0.625/0.375 | 0.125 | 542 | 35 |
| Example 2 | Two-layered tubular | InP | 1/0.5/0.625/0.375 | 0.125 | 544 | 37 |
| Example 3 | Two-layered tubular | InP | 1/0.5/0.625/0.375 | 0.03 | 548 | 32 |
| Example 4 | Two-layered tubular | InP | 1/0.5/0.375/0.375 | 0.03 | 570 | 48 |
| Example 5 | Two-layered tubular | InP | 1/0.5/0.5/0.375 | 0.03 | 565 | 41 |
| Example 6 | Two-layered tubular | InP | 1/0.5/0.75/0.375 | 0.03 | 552 | 45 |
| Example 7 | Two-layered tubular | In(Zn)P | 1/0.5/0.625/0.375 | 0.03 | 500 | 39 |
| Comparative Example 1 | T-shaped | InP | 1/0.5/0.375/0.375 | 1 | 573 | 50 |
| Comparative Example 2 | T-shaped | InP | 1/0.5/0.5/0.375 | 1 | 570 | 43 |
| Comparative Example 3 | T-shaped | InP | 1/0.5/0.625/0.375 | 1 | 550 | 39 |
| Comparative Example 4 | T-shaped | InP | 1/0.5/0.75/0.375 | 1 | 546 | 50 |
| Comparative Example 5 | Two-layered tubular | InP | 1/0.5/0.625/0.375 | 0.3 | 510 | 69 |
| Comparative Example 6 | T-shaped | In(Zn)P | 1/0.5/0.625/0.375 | 1 | 505 | 47 |

As shown in Table 1, in a case of comparing quantum dot dispersion liquids having the same elemental composition in the quantum dot dispersion liquid, it can be seen that the luminescence peak half-width can be narrowed and a quantum dot exhibiting sharper luminescence properties can be obtained in a case where the combining portion is constituted by a two-layered tubular mixer, and then the r2/r1 is set to satisfy the definition of the present invention, as compared to a case where the combining portion in the flow reaction is constituted by a T-shaped mixer (comparison of Comparative Example 1 and Example 4, comparison of Comparative Example 2 and Example 5, comparison of Comparative Example 3 and Examples 1 to 3, comparison of Comparative Example 4 and Example 6, and comparison of Comparative Example 6 and Example 7).

In addition, even in a case where a two-layered tubular mixer was used as a mixer constituting the combining portion, it was also found that the luminescence peak half-width was widely spread in a case where the r2/r1 was out of the definition of the present invention (comparison of Comparative Example 5 and Examples 1 to 3).

While the present invention has been described in conjunction with its embodiments, we do not intend to limit our invention in any detail of the description unless otherwise specified. It is to be understood that the present invention should be construed broadly without departing from the spirit and scope of the invention as set forth in the appended claims.

This application claims the priority of JP 2017-063603 filed in Japan on Mar. 28, 2017, the contents of which are incorporated herein by reference in its entirety.

EXPLANATION OF REFERENCES 100, 200: flow reaction system
1: first flow channel
2: second flow channel
3: combining region
3b: two-layered tubular mixer (multi-layered tubular mixer)
3c: three-layered tubular mixer (multi-layered tubular mixer)
A, B, C: opening
4: reaction flow channel
5, 6, 11: syringe
7: recovery container (flask)
10: third flow channel
T1: smallest tube (inner tube)
T2: outer tube
T3: middle tube
J: combining portion
H: electric furnace inside

What is claimed is:

1. A method for producing a Group semiconductor nanoparticle by a flow reaction, comprising:
   introducing a solution of compound a1 containing a Group III element into a first flow channel and introducing a solution of compound a2 containing a Group V element into a second flow channel;
   combining the solution of compound a1 flowing in the first flow channel and the solution of compound a2 flowing in the second flow channel in a combining portion; and
   reacting compound a1 and compound a2 while the combined liquid is flowing downstream to produce a Group III-V semiconductor nanoparticle,
   wherein the combining portion is constituted by a multi-layered tubular mixer,
   one of the solution of compound a1 and the solution of compound a2 is allowed to flow through a flow channel in the smallest tube of the multi-layered tubular mixer, and the other one of the solutions is allowed to flow through a flow channel adjacent to the flow channel in the smallest tube, and
   a value of a ratio of linear velocity r2 of the solution flowing in the flow channel adjacent to the flow channel in the smallest tube to linear velocity r1 of the solution flowing in the flow channel in the smallest tube is 0.2 or less.

2. The method for producing a Group III-V semiconductor nanoparticle according to claim 1, wherein the Group III element is selected from In, Al, and Ga.

3. The method for producing a Group III-V semiconductor nanoparticle according to claim 1, wherein the Group V element is selected from P, N, As, and Sb.

4. The method for producing a Group III-V semiconductor nanoparticle according to claim 1, wherein the Group III-V semiconductor nanoparticle is produced by setting the conditions for reacting compound a1 and compound a2 to 270° C. to 350° C. for 5 to 120 minutes.

5. The method for producing a Group III-V semiconductor nanoparticle according to claim 1, wherein the multi-layered tubular mixer is a two-layered tubular mixer.

6. The method for producing a Group III-V semiconductor nanoparticle according to claim 1, wherein an equivalent diameter of the smallest tube of the multi-layered tubular mixer is 0.1 to 2 mm.

7. A method for producing a Group III-V semiconductor quantum dot, comprising:
   obtaining a Group III-V semiconductor nanoparticle by the method for producing a Group III-V semiconductor nanoparticle according to claim 1; and
   introducing Ga into a surface layer of the Group III-V semiconductor nanoparticle.

* * * * *